United States Patent
Abdelghani et al.

(10) Patent No.: US 9,717,440 B2
(45) Date of Patent: Aug. 1, 2017

(54) SYSTEMS AND METHODS FOR DECODING INTENDED MOTOR COMMANDS FROM RECORDED NEURAL SIGNALS FOR THE CONTROL OF EXTERNAL DEVICES OR TO INTERACT IN VIRTUAL ENVIRONMENTS

(71) Applicant: The Florida International University Board of Trustees, Miami, FL (US)

(72) Inventors: Mohamed Abdelghani, Miami Beach, FL (US); Ranu Jung, Miami Beach, FL (US); James J. Abbas, Scottsdale, AZ (US); Kenneth Horch, Fountain Hill, AZ (US)

(73) Assignee: The Florida International University Board of Trustees, Miami, FL (US)

( * ) Notice: Subject to any disclaimer, the term of this patent is extended or adjusted under 35 U.S.C. 154(b) by 520 days.

(21) Appl. No.: 14/270,016

(22) Filed: May 5, 2014

(65) Prior Publication Data
US 2014/0330404 A1   Nov. 6, 2014

Related U.S. Application Data

(60) Provisional application No. 61/819,246, filed on May 3, 2013.

(51) Int. Cl.
*G05B 15/00* (2006.01)
*A61B 5/0488* (2006.01)
*A61B 5/0476* (2006.01)
*A61B 5/00* (2006.01)
*A61B 5/04* (2006.01)
(Continued)

(52) U.S. Cl.
CPC ...... *A61B 5/04888* (2013.01); *A61B 5/04001* (2013.01); *A61B 5/0476* (2013.01); *A61B 5/0488* (2013.01); *A61B 5/4851* (2013.01); *A61B 5/7203* (2013.01); *A61F 2/54* (2013.01); *A61F 2/72* (2013.01)

(58) Field of Classification Search
None
See application file for complete search history.

(56) References Cited

U.S. PATENT DOCUMENTS

| | | |
|---|---|---|
| 4,030,141 A | 6/1977 | Graupe |
| 4,209,860 A | 7/1980 | Graupe |

(Continued)

OTHER PUBLICATIONS

Abdelghani, Mohamed et al., "A computational model to simulate neural recordings from longitudinal intrafascicular electrodes," *Society for Neuroscience Conference*, 2012, 584.20/SS19. Abstract.

(Continued)

*Primary Examiner* — Adam Lee
(74) *Attorney, Agent, or Firm* — Saliwanchik, Lloyd & Eisenschenk

(57) ABSTRACT

Systems and methods for decoding neural and/or electromyographic signals are provided. A system can include at least one single channel decoder. Optionally, the system can include a demixer in operable communication with the single channel decoders. Each single channel decoder can include a filter to attenuate noise and sharpen spikes in the neural and/or electromyographic signals, a detection function to identify spikes, and a demodulator to get a real-time estimate of motor intent.

17 Claims, 17 Drawing Sheets

(51) Int. Cl.
A61F 2/72 (2006.01)
A61F 2/54 (2006.01)

(56) References Cited

U.S. PATENT DOCUMENTS

| | | | | |
|---|---|---|---|---|
| 4,603,703 | A * | 8/1986 | McGill | A61B 5/04525 600/544 |
| 4,782,387 | A * | 11/1988 | Sabri | H04N 19/50 341/88 |
| 4,888,641 | A * | 12/1989 | Isnardi | H04N 11/004 348/E11.003 |
| 5,216,752 | A | 6/1993 | Tam | |
| 5,336,269 | A * | 8/1994 | Smits | A61F 2/72 623/24 |
| 5,581,665 | A * | 12/1996 | Sugiura | B25J 9/1607 345/419 |
| 5,631,553 | A * | 5/1997 | Bose | G01R 19/2506 324/76.23 |
| 5,751,888 | A * | 5/1998 | Fukuchi | H04N 19/51 375/E7.094 |
| 5,926,791 | A * | 7/1999 | Ogata | H04N 19/63 375/240.11 |
| 6,144,409 | A * | 11/2000 | Han | G06T 9/20 348/426.1 |
| 6,151,278 | A * | 11/2000 | Najarian | G04B 25/04 368/12 |
| 7,058,445 | B2 | 6/2006 | Kemere et al. | |
| 7,442,212 | B2 | 10/2008 | Richmond et al. | |
| 8,332,024 | B2 | 12/2012 | Rapoport et al. | |
| 8,352,385 | B2 | 1/2013 | Rapoport et al. | |
| 8,386,050 | B2 | 2/2013 | Donoghue et al. | |
| 8,756,183 | B1 * | 6/2014 | Daily | G06N 3/049 706/20 |
| 2002/0131583 | A1 * | 9/2002 | Lu | H04B 3/23 379/406.08 |
| 2003/0023319 | A1 * | 1/2003 | Andersen | A61F 2/68 623/24 |
| 2003/0185408 | A1 * | 10/2003 | Causevic | A61B 5/04845 381/94.1 |
| 2005/0021103 | A1 * | 1/2005 | DiLorenzo | A61N 1/3605 607/45 |
| 2005/0113049 | A1 * | 5/2005 | Takayama | H04H 20/22 455/150.1 |
| 2005/0113703 | A1 * | 5/2005 | Farringdon | A61B 5/0428 600/509 |
| 2005/0159668 | A1 * | 7/2005 | Kemere | A61B 5/0476 600/544 |
| 2006/0229878 | A1 * | 10/2006 | Scheirer | G10H 1/0008 704/273 |
| 2007/0064940 | A1 * | 3/2007 | Moskowitz | G06F 21/10 380/205 |
| 2008/0294579 | A1 * | 11/2008 | Rapoport | A61B 5/04001 706/12 |
| 2009/0024395 | A1 * | 1/2009 | Banba | G10L 19/0204 704/500 |
| 2009/0180351 | A1 * | 7/2009 | Paffenholz | G01V 1/364 367/38 |
| 2009/0326406 | A1 * | 12/2009 | Tan | G06F 3/015 600/546 |
| 2010/0250242 | A1 * | 9/2010 | Li | G10L 17/02 704/200.1 |
| 2010/0305647 | A1 * | 12/2010 | McCabe | A61B 5/04001 607/18 |
| 2011/0103444 | A1 * | 5/2011 | Baum | G10L 19/018 375/224 |
| 2013/0073065 | A1 * | 3/2013 | Chen | G10L 19/018 700/94 |
| 2014/0058528 | A1 * | 2/2014 | Contreras-Vidal | A61B 5/04842 623/25 |

OTHER PUBLICATIONS

Abdelghani, Mohamed et al., "Decoding motor intent from simulated multiple longitudinal intrafascicular electrode recordings," 22$^{nd}$ Annual Computational Neuroscience Meeting, 2013, p. 1-2.

Clark, G.A., et al., "Recording sensory and motor information from peripheral nerves with Utah Slanted Electrode Arrays," 33$^{rd}$ Annual International Conference of the IEEE EMBS, 2011, 4641-4644.

Dhillon, G.S., et al., "Direct neural sensory feedback and control of a prosthetic arm," IEEE Transactions on Neural Systems and Rehabilitation Engineering, 2005, 13(4):468-472.

Dhillon, G.S., et al., "Residual function in peripheral nerve stumps of amputees: Implications for neural control of artificial limbs," Journal of Hand Surgery, 2004, 29(4):605-615.

Hallin, Rolf G., "Microneurography in relation to intraneural topography: somatotopic organization of median nerve fascicles in humans," Journal of Neurology, Neurosurgery, and Psychiatry, 1990, 53:736-744.

Jiang, Ning et al., "Extracting Simultaneous and Proportional Neural Control Information for Multiple-DOF Prostheses From the Surface Electromyographic Signal," IEEE Transactions on Biomedical Engineering, 2009, 56(4): 1070-1080.

Kuiken, Todd a., et al., "Targeted Muscle Reinnervation for Real-time Myoelectric Control of Multifunction Artificial Arms," JAMA, 2009, 301(6): 619-628.

Micera, Silvestro et al., "Decoding of grasping information from neural signals recorded using peripheral intrafascicular interfaces," Journal of NeuroEngineering and Rehabilitation, 2011, 8(53).

Micera, Silvestro et al., "On the Use of Longitudinal Intrafascicular Peripheral Interfaces for the Control of Cybernetic Hand Prostheses in Amputees," IEEE Transactions on Neural Systems and Rehabilitation Engineering, 2008, 16(5): 453-472.

Rehbaum, Hubertus et al., "Real time simultaneous and proportional control of multiple degrees of freedom from surface EMG: Preliminary results on subjects with limb deficiency," 34$^{th}$ Annual International Conference of the IEEE EMBS, 2012, 1346-1349.

Wodlinger, Brian et al., "Localization and Recovery of Peripheral Neural Sources With Beamforming Algorithms," IEEE Transactions on Neural Systems and Rehabilitation Engineering, 2009, 17(5):461-468.

* cited by examiner

A) Examples of orthogonal or non-overlapping motor intent signals and estimates

B) Examples of neural recordings by two electrodes

SYSTEMS AND METHODS FOR DECODING INTENDED MOTOR COMMANDS FROM RECORDED NEURAL SIGNALS FOR THE CONTROL OF EXTERNAL DEVICES OR TO INTERACT IN VIRTUAL ENVIRONMENTS

CROSS REFERENCE TO RELATED APPLICATION

The present application claims the benefit of U.S. Provisional Application Ser. No. 61/819,246, filed May 3, 2013, which is hereby incorporated by reference herein in its entirety, including any figures, tables, and drawings.

GOVERNMENT SUPPORT

This invention was made with government support under a grant awarded from the Defense Advanced Research Projects Agency (DARPA) under grant number N66001-12-C-4195. The government has certain rights in this invention.

BACKGROUND OF INVENTION

Decoding motor intent from recorded neural signals is essential for the development of effective neural controlled prostheses. The motor intent signal provides information on the class of intended movement, such as hand opening and the degree of the intended movement (e.g., half-way or fully-opened hand). The design, development, and control of prostheses with biological signals have been extensively researched. For the purpose of control of powered prostheses, a wide variety of decoding algorithms have been developed using biological signals such as electroencephalograms (EEG), electromyogram (EMG), or neural signals detected by cortical and peripheral interfaces. The decoding algorithms differ depending on the types of biological signals recorded, the design and properties of machine tissue interfaces, the design and function of prostheses, and the extent of injury (e.g. amputation, paralysis, etc.).

For example, a transradial amputee with some residual function in wrist flexor extensor muscles can be, with surface EMG recording, fitted with a one degree-of-freedom myoelectric controlled hand. In this case, the decoding algorithm is simple; it involves the filtering of EMG signals to eliminate noise and crosstalk, followed by rectifying and low-pass filtering the resultant signal to obtain a control signal to derive motors of the prosthesis. Though this kind of myoelectric control of prostheses is widely used and its decoding method simple, it has a number of limitations. Its control is limited to one degree of movement at a time, and changes in surface EMG electrodes impedance and position alter recorded EMG signals and degrade control of the prosthesis. Also, this method of control is dependent on the availability of remainder muscles, and is therefore limited to low-level amputation. Thus, this type of surface EMG control cannot provide appropriate information to control many lost degrees of freedom.

Recently, a new surgical procedure was developed to ameliorate the problems of recording EMG from residual muscles in amputees. The procedure is known as target muscle re-innervation (TMR) (Kuiken et al. 2010). A target muscle of an amputated patient is de-nervated (its original nerves cut) then re-innervated with residual nerves of the amputated limb. With many surface EMG electrodes, the problem of high level amputation can be addressed using this surgical technique, but the surgical procedure is complicated. Also, the decoding algorithms have become more complicated. Using a linear classifier, the decoder can identify the movement class, whether it's a power grip, hand opening and closing, or other class. The prosthetic arm used in this experiment was self-actuated. The amputee is only required to intend a single motion class (e.g., hand grip), and the rest of the actuation of the prosthesis is handled by the mechatronics of the prosthesis. One limitation with this approach is that the user is not able to control the degree by which to open or close their hand or to control how fast or slow the robotic arm moves; i.e., the user does not have the ability to execute graded control of the actuation of the prosthesis.

An alternative to EMG recording is recording neural activity from either the central nervous system (CNS) or the peripheral nervous system (PNS). Recently, the number of devices to interface with CNS and PNS has seen a dramatic increase due to advances in fabrication methods. CNS interfaces provide direct access to cortical or spinal cord neurons while peripheral interfaces provide access to afferent and efferent axons signals. Many CNS interfaces and PNS interfaces have different designs and functionality. Some interfaces are not invasive, such as electroencephalography (EEG) while others are invasive like penetrating electrode arrays and longitudinal intrafascicular electrodes (LIFEs). Noninvasive electrodes tend to be less specific and record average activity from a large population of neurons while invasive electrodes tend to be more specific, recording from only a few related neurons. With the increase in neural interfaces, a variety of decoding techniques have been developed.

In a recent study, a monkey was implanted in the arm area of the primary motor cortex with a 100-electrode silicon array (Wood et al. 2004). The monkey was trained to use a two-joint planar manipulandum to control the motion of a cursor on a computer screen. Hand kinematics and neural activity were recorded to study cortical encoding of hand motion. Recorded spike data was automatically sorted in the following way: first, data dimensionality was reduced by principle component analysis (PCA); then, an expectation maximization algorithm using a mixture of Gaussians was used for classification. In another study, a monkey was implanted with a single 96-channel array in the primary motor cortex (Fraser el al. 2009). Again, the objective was to have the monkey control a cursor movement on a screen. By setting a single threshold across all channels and fitting the resultant events with a spline tuning function, a control signal was extracted from this population using a Bayesian particle-filter without the need for spike sorting. Spike sorting was shown to not be necessary for high quality neuroprosthetic control.

To record from peripheral nerves, many electrode interfaces have been devised. Some common ones are nerve CUFF, FINE, LIFE, tLIFE, and penetrating electrode arrays. The different electrodes vary in terms of their level of invasiveness and signal selectivity, detection sensitivity, and purity of signals recorded. On the peripheral side, many algorithms have been developed for decoding neural activity. A 16-channel tripolar flat interface nerve electrode (FINE), a variant of the CUFF electrode, was used to record rabbits (Wodlinger et al. 2011). The beam-forming algorithm was used to recover signals from the sciatic nerve while the distal tibial and peroneal branches were stimulated. The beam-forming algorithm is a spatial filter that is able to distinguish which branch was being stimulated and how strongly, and therefore which muscles will be active. A 100-electrode Utah Slanted Electrode Arrays (USEAs) was used to record from feline sciatic nerve (Clark et al. 2011).

After spike sorting, part of the neural data was used to train an offline optimal linear regression filter to relate spike counts to ankle joint angle in one plane.

A computational study compared different types of firing rate estimation methods, time-domain features (e.g. spike-duration, zero-crossing), and spike counting combined with a linear classifier, to decode simulated neural recording from UTAH arrays (Zhou el al. 2010). Thin film intrafascicular electrodes have been used to record neural activity from animal and human amputees (Micera et al. 2010). Signals were processed by wavelet de-noising followed by a spike classification stage. After spike classification, a support vector machine classifier was used to relate motor intent to neural firing. The intended movements were used to derive a finite state machine that controls a powered prosthesis. Both of these studies provide methods for identifying a class of movement, but do not provide a means for real-time graded control of the prosthesis. It has been shown that LIFEs can be used to record from peripheral nerves in amputees and control a robotic arm in a graded fashion, but only with one degree-of-freedom (Dhillon et al. 2004, 2005).

U.S. Pat. No. 8,352,385 discloses a low power analog chip to decode neural activity from cortical neurons into motor control parameters. The chip implements multiple channels of recording and uses a set of tunable parameter linear filters. However, the decoding algorithm assumes that each channel is independent and that during the tuning phase the mean firing rate is available for each channel. U.S. Pat. No. 7,442,212 describes a method by which recorded neural activity from many electrodes during a motor task is used to calculate a cumulative total spike density function in multiple dimensions. The spike density functions are used as instructions to control a prosthetic limb. This method relies on order statistics and is therefore computationally cumbersome and requires extensive computational power. Furthermore, it only identifies classes of movement and does not provide any real-time graded motor control. U.S. Pat. No. 7,058,445 is another cortical decoding scheme to control a machine. This technique uses activity from two different phases of neural activity during an intended movement. The first phase is known as the peri-movement information while the second phase is known as the movement phase. The estimated motor activities from the two phases are combined in an "optimal way" to produce a control signal. This scheme uses a point process filter to approximate non-stationary firing-rate. The method is based on switching between minimum and maximum firing rate and does not try to track the actual firing rate; rather, it approximates the firing rate by switching between maximum and minimum rates.

Thus, a variety of decoding algorithms have been used with varying degrees of success in animal and human trials. All these decoders use an assortment of signal processing techniques (band-pass filtering, wavelet-de-noising, Kalman and Wiener filters, adaptive filtering) and machine learning techniques (support vector machines, bayesian estimation). Some decoders are complex but general while others are more specialized and simple. Some decoders are fast while others are slow. Some decoders are reliable but limited while other are versatile but less accurate. Most decoders are able to produce only categorical output with a few able to do graded control when the input signals are independent and there is no cross-talk between channels. While the majority of these decoders have been implemented in software, there are some that have been implemented in specialized signal processing hardware or custom integrated circuits.

BRIEF SUMMARY

Embodiments of the subject invention provide systems and methods to decode intended motor actions from recorded neural signals and/or electromyographic (EMG) signals (which can collectively be referred to as "input signals" for convenience). For example, systems and methods of the subject invention can determine class of action and degree of action based on recorded neural signals and/or muscle signals. Systems and methods of the subject invention relate to the use of neural signals and/or muscle signals to control one or more external devices (e.g., powered prostheses, televisions, computers, portable electronics, or other external appliances). In many embodiments, neural signals and/or muscle signals of intended actions are trained to motor command signals appropriate for the control of powered prostheses (e.g., a robotic hand).

Embodiments of the subject invention provide systems and methods to decode intended motor actions from neural signals and/or muscle signals recorded by multiple neural interface electrodes. The systems and methods can operate in real-time and be implemented in a portable, low-power configuration. The systems and methods can interpret signals from a single or multiple electrodes to enable single or multiple degree-of-freedom control of a powered prosthesis. In an embodiment, the intended motor action includes the intended class of action and the intended degree of action. In a particular embodiment, de-noising of the input signals is achieved by a bank of band pass filters that may be tunable and that may use wavelets with several thresholding criteria. In a further embodiment, a nonlinear reshaping function is used to detect spikes, to suppress noise, and/or to normalize spike amplitudes. In yet a further embodiment, a tunable demodulator is implemented to estimate motor intent signals, and the time constant of the demodulator can be tuned based on the rate of change of the current estimate of the motor intent.

In an embodiment, an adaptive learning architecture can be used to enable the systems and methods to automatically learn, in real-time or off-line mode, to decode motor intent from recorded neural signals and/or muscle signals. The intended motor action can be used to control an external powered appliance, such as a single or multiple degree-of-freedom robot. The intended motor action can be used in an interactive computing environment (e.g., to control an avatar). Systems and methods of the subject invention can be used to assess muscle activity and neuron function during nerve stimulation and/or regional anesthesia. Systems and methods of the subject invention can include one or more single channel decoder that downsamples and compress the recorded neural signal or muscle signal to allow for faster and more efficient transmission from the decoder to the controlled device or interactive computing environment. In many embodiments, a system for decoding intended motor actions from neural signals and/or muscle signals recorded by one or more electrodes includes: at least one single channel decoder (SCD); and, optionally, a demixer in operable communication with the at least one SCD.

DETAILED DISCLOSURE

Figure 1:
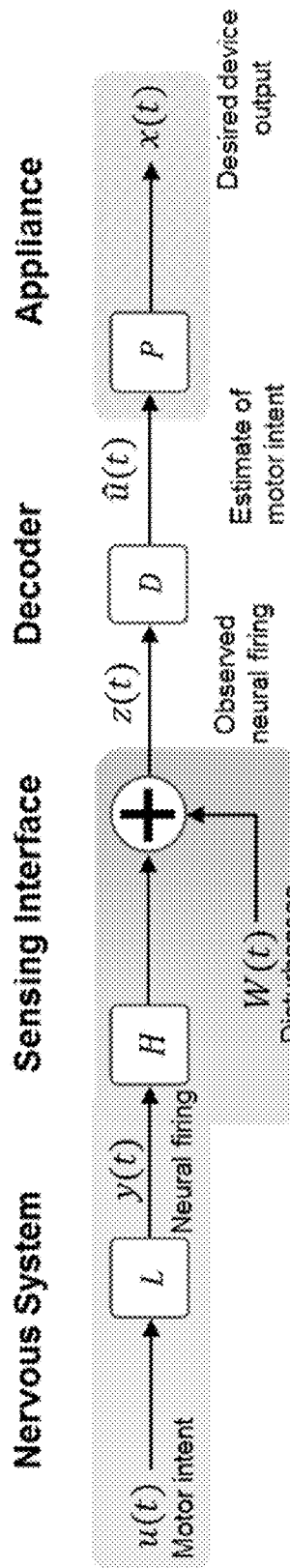
FIG. 1 shows a diagram of a decoder according to an embodiment of the subject invention.

Embodiments of the subject invention provide systems and methods to decode intended motor actions from recorded neural signals and/or muscle signals (which can collectively be referred to as "input signals" for convenience). For example, systems and methods of the subject invention can determine class of action and degree of action based on recorded neural signals and/or muscle signals. Systems and methods of the subject invention relate to the use of neural signals and/or muscle signals to control one or more external devices (e.g., powered prostheses, televisions, computers, portable electronics, or other external appliances). In many embodiments, neural signals and/or muscle signals of intended actions are trained to motor command signals appropriate for the control of powered prostheses (e.g., a robotic hand).

In many embodiments, a system is a decoder including a demixer and at least one single channel decoder (SCD). The demixer and the SCDs are in operable communication with each other. In certain embodiments, the demixer is not present. For example, a single-channel system can include one SCD (with no demixer) or a multiple-channel system can include several channels each with its own SCD (with no demixer), such that the cross-talk between channels is insignificant.

As used herein, and unless otherwise specifically stated, the terms "operable communication" and "operably connected" mean that the particular elements are connected in such a way that they cooperate to achieve their intended function or functions. The "connection" may be direct or indirect, physical (e.g., by wires or other physical connections) or remote (e.g., wireless).

In an embodiment, a system has two phases of operation: configuration phase and online decoding phase. In the configuration phase, the decoder is initialized and trained to associate neural activity to the corresponding motor intent. In the online decoding phase, the system decodes neural activity in real time. The inputs to the system can be neural recordings (e.g., from a single- or multi-electrode neural interface). In some embodiments, additional input of associated behavioral responses measured by sensors is used. In certain embodiments, behavioral responses are required during the configuration phase of the system.

In an embodiment, the output of the system is a signal or an array of signals to control one or more external devices (e.g., a powered prosthesis). The system can include a decoder, which can include: multiple SCDs; a demixer; and a decoder configuration unit. The SCD decodes motor intent from neural recordings from a single electrode. The (or each) SCD can include: a filter to attenuate noise and sharpen spikes in the neural recordings of nerve firing; a detection function to identify spikes; and a demodulator to get a real-time estimate of motor intent. The demixer can identify the motor intent signals as corresponding to a particular class of movement, for example, wrist flexion, supination, or other types of movement. The demixer's inputs can be from the SCDs. The outputs can be signals to control one or more external devices. During the configuration phase, the decoder configuration unit can train the demixer to interpret recordings of multiple electrodes to different classes of movement, as well as the degree of movement. In an embodiment, the demixer can be implemented as a single learning algorithm or an array of learning algorithms, for example, artificial neural networks, support vector machines, or other learning algorithms. A simple linear method in the parameter learning, such as a batched Least Mean Square (LMS) algorithm, can be used to train the parameters of the demixer to produce appropriate control signals. In certain embodiments, the SCDs and the demixer can be implemented, individually or together, in software, firmware, or hardware.

There is much room for improvement in the art of decoding neural data. The ability to control an external appliance in real-time with multiple degrees of freedom in a graded fashion using neural data recorded from multiple electrodes is still open for improvement. The key requirements for successful neural decoding for real-time use include: estimated motor intent must be reliable and output noise minimal, even if inputs are noisy; decoding must be performed in real-time with minimal delay; decoding algorithms must be implementable in hardware; decoded motor intent must match motor intent in terms of the level of effort and the action intended (i.e., the decoded signal must be intuitive to the user; decoder must be able to produce graded motor signals and not just categorical outputs.; and decoder must be robust and tunable to compensate for errors as a result of degraded neural recording and noise. Systems and methods of the subject invention advantageously meet all of these requirements for successful neural decoding for real-time use.

Embodiments of the subject invention provide systems and methods for decoding neural activity from recordings made by a neural interface of one or more electrodes (e.g., a system of multiple electrodes). Such a decoder system can estimate motor intent (e.g., class of action and degree of action) willed by a subject using recorded neural activity of the subject. Decoders of the subject invention can be used with a variety of multiple electrode systems, including but not limited to cortical interfaces and peripheral interfaces such as cortical arrays, UTAH arrays, and longitudinal intrafascicular electrodes (LIFEs).

Neural recordings obtained by neural interface electrodes should satisfy certain criteria for the motor intent estimation to be reliable and effective. First, the information content of neural activity recorded by the neural interface must be sufficient for decoding the required motor intent signals. For example, recording from radial and ulnar nerve in an upper level amputee may only allow decoding of wrist flexion and extension movement but not any elbow movement. Second, some level of specificity is required where spikes can be identified and the degree of superposition between spikes is small. Third, the signal to noise ratio in any channel of recording during any level of activity must exceed a minimum level pre-determined during initial assessment of the quality of the recorded signal. Fourth, motor intent signals must be easily and reliably measured to train the decoder during the configuration phase.

Embodiments of the subject invention provide systems and methods for decoding neural activity to the corresponding motor intent. The decoding system can include multiple single channel decoders (SCDs), a demixer, and a unit to configure the decoder. An SCD can decode motor intent from recordings from a single electrode. Each SCD can include a filter to attenuate noise and sharpen spikes, a detection function to identify spikes, and a demodulator to obtain a real-time estimate of motor intent. Each SCD can be equipped with online tunable parameters. The demixer can identify the motor intent signals as corresponding to a particular motion class (e.g., wrist flexion, supination, or other movement), for example in situations where the outputs from one or more SCDs contain signal components derived from more than one motor intent signal. The demixer's inputs can be all the SCD outputs and during the configuration phase can also include additional reference motor intent signals. During the configuration phase, the decoder configuration unit can train the demixer to interpret recordings of multiple electrodes to different classes of movement (i.e., segregate mixed motor intent signals) and the degree of movement. The decoder can be operated in online operation mode where the output (estimated motor intent) is used to control, for example, a device or a cursor on a screen, using the learned map established in the configuration phase.

In an embodiment, a decoder is designed to obtain real time estimates of motor intent signals. The decoder can be implemented in software (e.g., MATLAB) and/or specialized signal processing hardware (e.g., signal processing hardware by Tucker-Davis-Technologies using their Real-Time Processor Visual Design Studio). In a further embodiment, a decoder can also be implemented in a mixed signal Very Large Scale Integrated (VLSI) circuit design.

In an embodiment, a decoder is equipped with an optional spike sorting unit to detect and sort spikes. The spike sorting unit can be configured during the configuration phase of the decoder. Spike sorting is essential if there is a high degree of crosstalk between channels of the neural interface.

In an embodiment, units of the decoder are essentially independent and can be distributed on specialized devices. For example, the SCD can be implemented in an implanted chip while the demixer is on external signal processing hardware. The output of a SCD can be of much lower frequency than the recorded input neural activity and can therefore be down-sampled and compressed for faster, more efficient transmission from decoder to external device using different communication modalities, including but not limited to radio frequency (RF) link.

Embodiments of the subject invention provide systems and methods designed to achieve real-time decoding of graded levels of motor intent (class of action and degree of action) from neural signals and/or muscle signals obtained by single or multiple recording electrodes. Major aspects of the system include a set of SCDs and, optionally, a demixer. The decoding system can utilize methods from signal processing that are assembled in an advantageous way to obtain a real-time, accurate estimate of the motor intent signals. Aspects of the subject invention include, but are not limited to: implementation of a bank of band-pass filters to attenuate noise and enhance spikes; implementation of nonlinear functions to suppress noise and reshape and normalize spikes; implementation of demodulators using a variety of smoothing kernels to convert spike trains to motor intent signals—the parameters of the smoothing kernel can be tunable on the basis of the rate of change of the output of the demodulator; and implementation of adaptive linear/nonlinear filters endowed with learning rules (e.g., LMS, gradient descent) to map outputs of SCDs to desired motor control signals. The band-pass filters, nonlinear functions, and smoothing kernels can be components of SCDs. The adaptive filters can be used to implement the demixer. The SCDs together with a demixer can constitute the main units of the decoding system.

FIG. 1 is a diagram of a decoder according to an embodiment of the subject invention. In a neuro-control system, the function of the decoder can be to map neural signals and/or muscle signals to motor intent signals. It can be a link between the neural electrode interface and powered appliances. Referring to FIG. 1, u is a motor intent vector; y is a neural firing vector; L is a function that transforms motor intent u to neural firings y. H is a function that transforms neural firings of neurons to recorded neural signals (and/or muscle signals) z observed by the sensing electrodes. D is the decoder function; it reconstructs the best estimate u-hat of u from sensed information z. As used herein, the designation "-hat" after a variable indicates that the variable would normally be written with a "^" over it. P is a function that encapsulates primary functions of an external device (e.g., prosthesis, iPhone, computer, other electronic device) and transforms the estimate of motor intent to desired outputs. x is desired device output (e.g., reach to apple, click icon on screen, etc.).

FIG. 1 shows a system-level description of the placement of the decoder in the neuro-motor device chain. u(t) is an n×1 motor intent vector; y is an m×1 vector of neural firings; L is a function that transforms motor intent u to neural firings y. L is considered to be a collection of Poisson processes whose means are modulated by motor intent signals y. H is a mapping that transforms neural firings of neurons to recorded neural signals (and/or muscle signals) z observed by the sensing electrodes. Since electric fields emanating from action potentials that are picked up by electrode systems sum linearly, H may be approximated by an/x m matrix. z is an l×1 vector of recorded neural activities. W is ambient noise in biological media and electronic recording devices associated with the neural interface. W can be approximated as 1/f noise. D is the decoder function; it reconstructs the best estimate u-hat of u from sensed information z. u-hat is not necessarily an n×1 but a k×1 vector where k≤l≤n≤m. P is a function that encapsulates functions of external, devices and transforms the estimate of motor intent to desired outputs x.

In the following paragraphs, the decoder design and functionality are described in detail and an example is given of a decoder specifically implemented to decode motor intent signals from associated neural recordings obtained by multiple longitudinal intrafascicular electrodes (LIFEs). The results and testing were done using simulated neural recordings.

Figure 2:
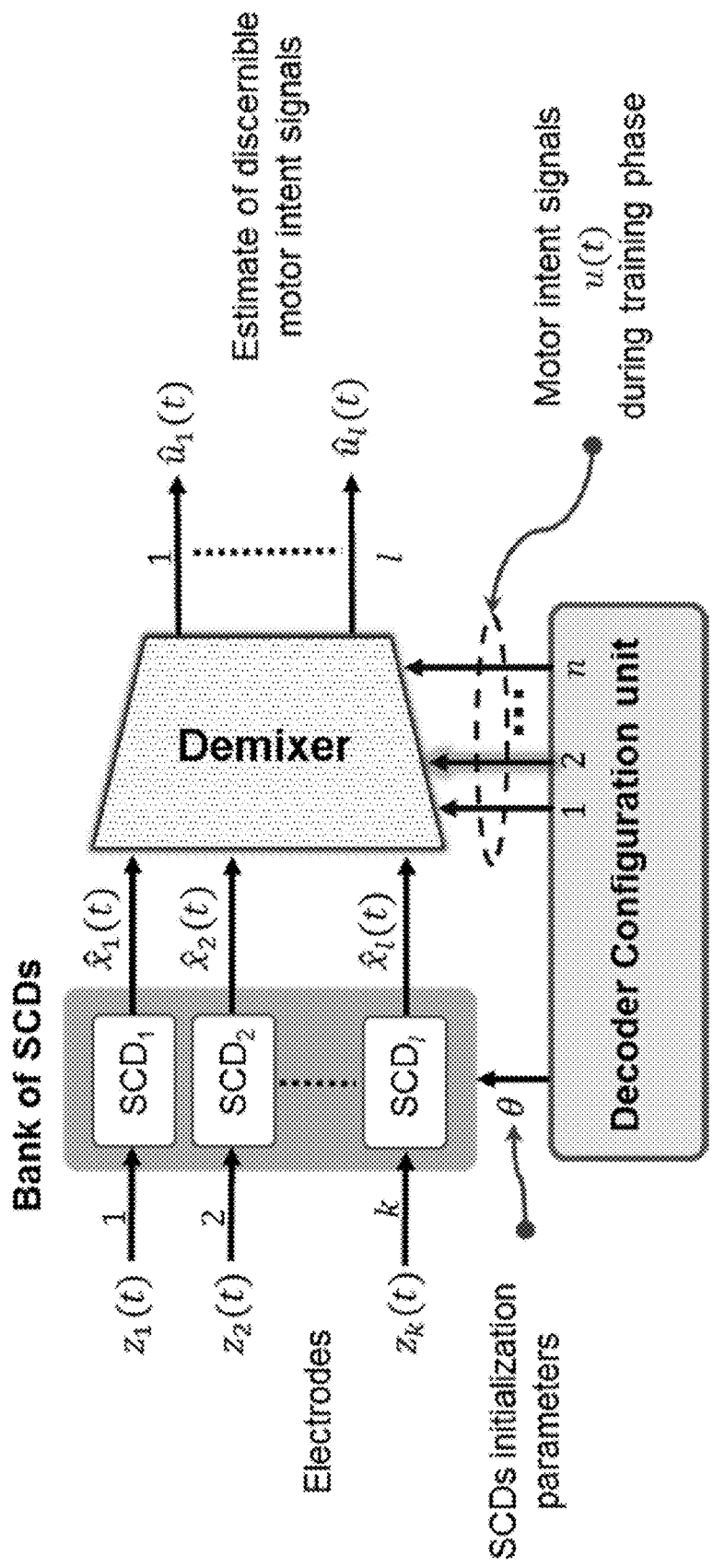
FIG. 2 shows a diagram of a decoder according to an embodiment of the subject invention.

FIG. 2 is a diagram of a decoder according to an embodiment of the subject invention, showing a multi-channel decoder (MCD) design. An MCD can include a bank of SCDs, a demixer, and a decoder configuration unit. SCDs decode motor intent from neural recordings from a single electrode. The demixer identifies the motor intent signals as corresponding to a particular motion class. The demixer requires a learning stage, where recordings from electrodes are correlated to motion classes. It is the job of the decoder configuration unit to tune the parameters of the demixer, for example, by a simple batched LMS algorithm. The configuration unit computes the SCD initialization parameter, such as detector thresholds and filter parameters.

The decoder can include a bank of SCDs, a demixer, and a unit to configure the system (FIG. 2). The single channel decoder decodes neural activity recorded by a single electrode in an unsupervised manner. The demixer identifies and sorts decoded motor intent signals into appropriate motion classes and also rescales the signals to their appropriate amplitudes. The demixer requires a training stage which takes place during the configuration phase. The decoder configuration unit is responsible for the decoder configuration phase. In the configuration phase, the decoder cycles over a specific set of vectors of motor intent signals and obtains the associated neural activity. In this phase, recorded neural signals and/or muscle signals are analyzed, single channel decoder initialization parameters are set (e.g., thresholds and time constants), and the demixer is trained (e.g., by batched LMS or gradient descent algorithm) by relating the classes of motor intent signals to the resultant neural activity. In certain embodiments, the vectors of motor intent signals can be orthogonal and/or the classes of motor intent signals that are related to the resultant neural activity can be orthogonal.

The computational modeling and simulation of multiple LIFEs was the subject of a provisional patent application (U.S. Provisional Patent Application Ser. No. 61/714,578, filed Oct. 16, 2012, for "Simulator of Neural Activity Patterns and Recordings of those Patterns from Electrodes", by Abdelghani et al.). The content of this provisional patent application are hereby incorporated by reference in its entirety.

Figure 3:
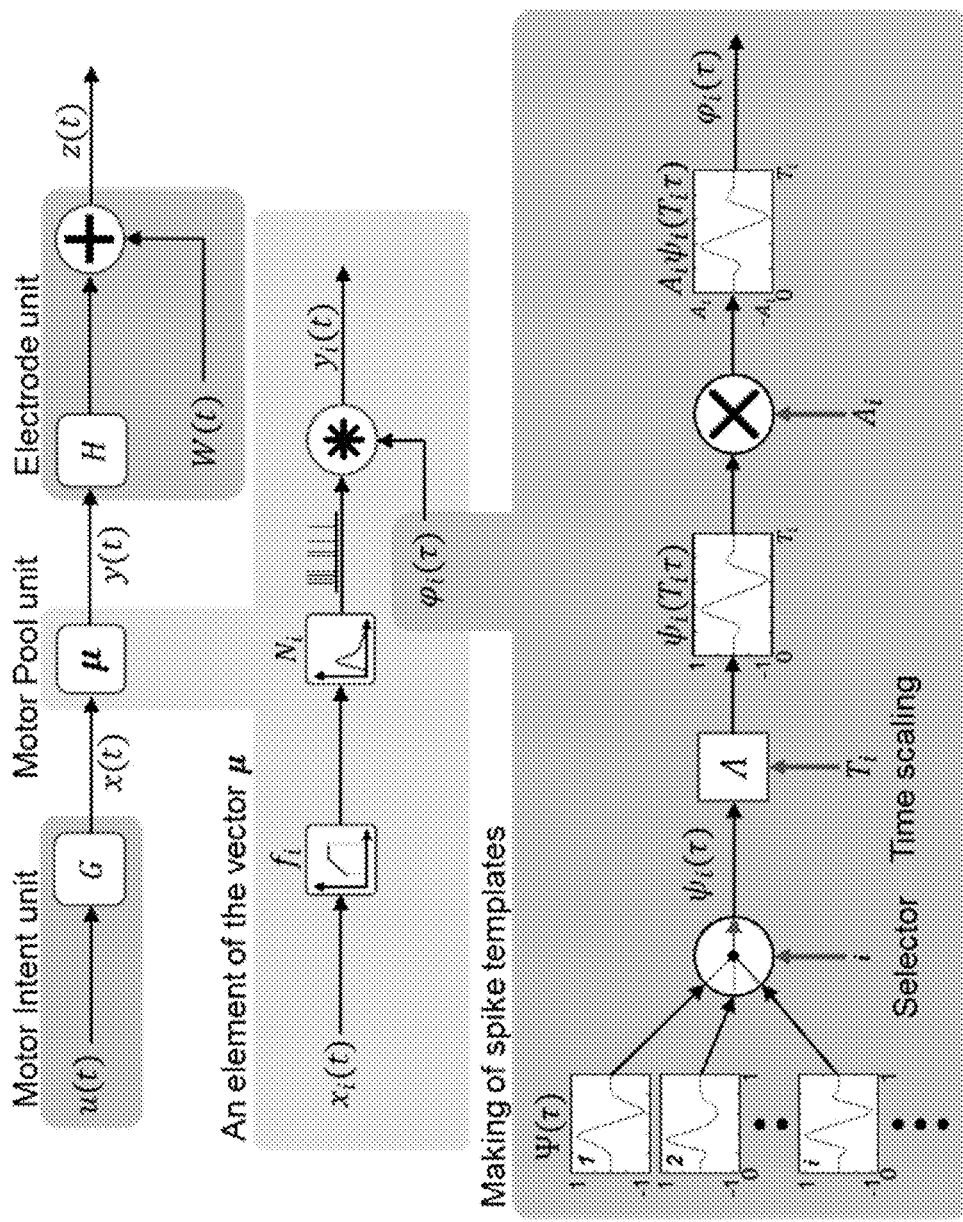
FIG. 3 shows a diagram of a simulator design for neural interface recording electrodes according to an embodiment of the subject invention.

In an embodiment, LIFEs can be used for recording activity from peripheral nerves. LIFEs can be used in human amputees for multiple degree of freedom control of prostheses. To test the viability of decoding algorithms to estimate multiple motor intents from multiple LIFEs, a platform was developed to simulate recording of extracellular motor activity from multiple LIFE electrodes, as shown in FIG. 3.

Figure 9:
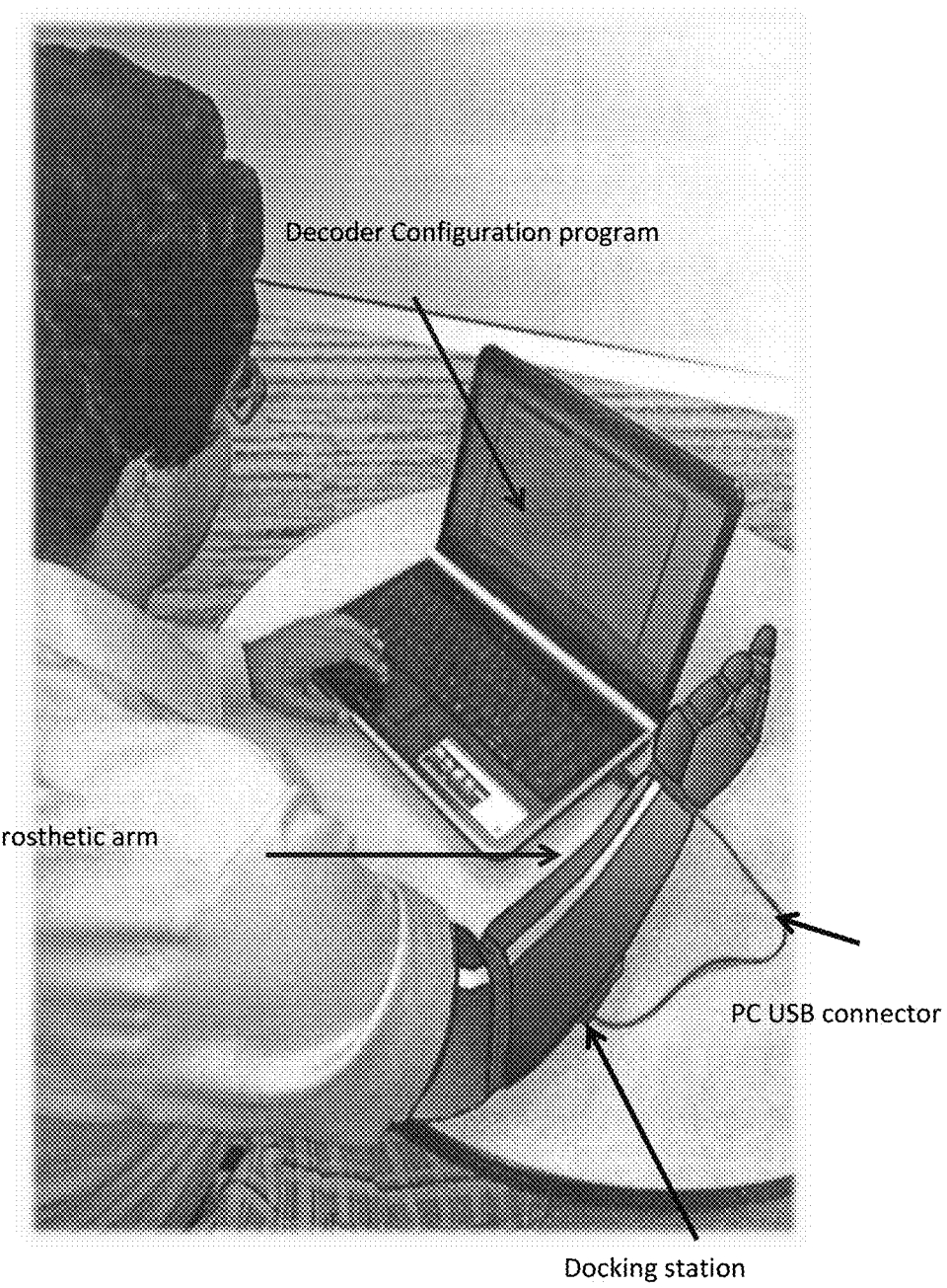
FIG. 9 shows a diagram of a portable reconfiguration of a decoder according to an embodiment of the subject invention.

FIG. 9 shows a diagram of a portable reconfiguration of a decoder according to an embodiment of the subject invention. A decoder configuration unit can be supported by a decoder configuration program that can run on any computing device, for example, a portable computing device such as a laptop. The decoder configuration program can tune the prosthesis whenever it is not performing what the user desires. For example, it is possible that after a long term use of the prosthesis the response of the prosthesis may not match user-intended action, which could be due to mechanical, electrical, environmental, or biological reasons. In this case, the user can reconfigure the operation of the prosthesis. FIG. 9 shows a user fitted with a powered prosthetic arm connected to a laptop. A program Decoder Configuration Program (DCP) running on the laptop can guide the user in a step-by-step way to reconfigure the arm.

Figure 10:
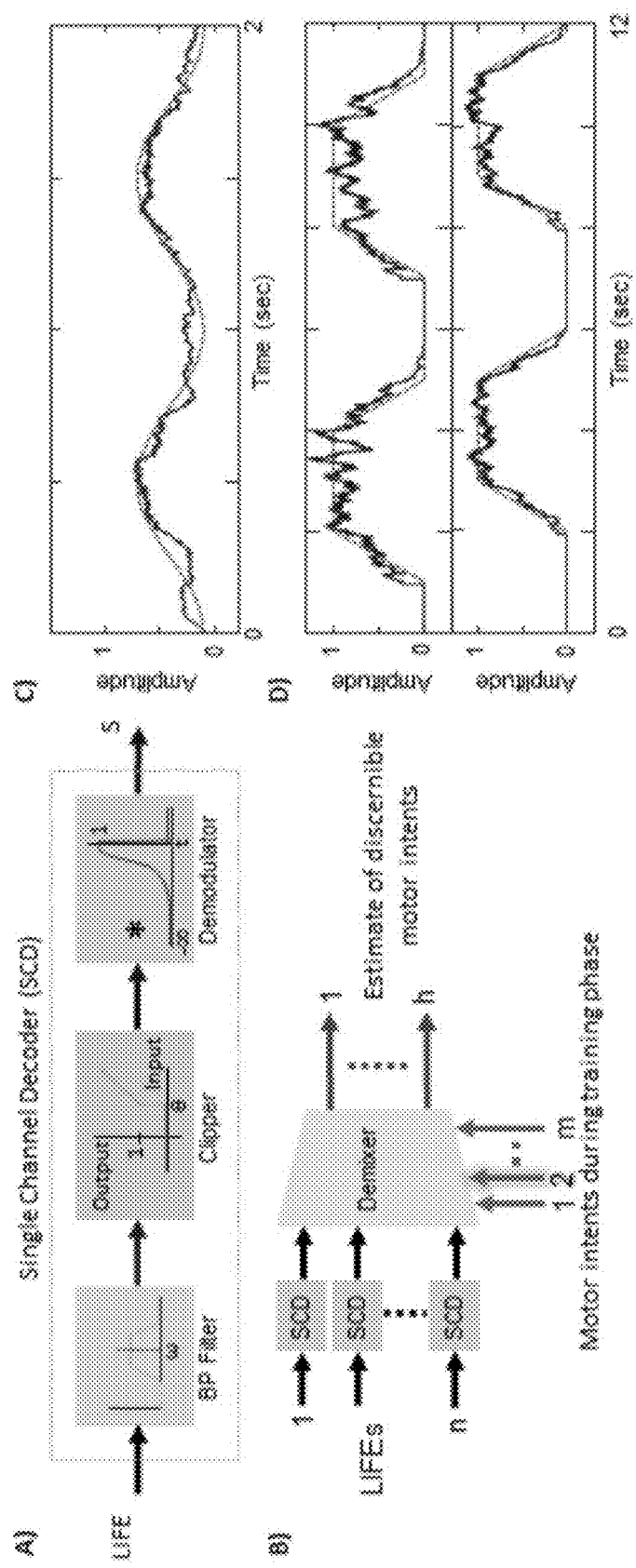
FIG. 10A shows a schematic of a SCD according to an embodiment of the subject invention.
FIG. 10B shows a schematic of multiple SCDs and a demixer according to an embodiment of the subject invention.
FIG. 10C shows a plot of actual motor intent and decoded motor intent.
FIG. 10D shows a plot of demixing of two overlapped motor intents.

FIG. 10A shows a schematic of a LIFE SCD. Neural signals and/or muscle signals can be bandpass filtered, clipped to remove any residual background noise and normalize spike amplitudes, and filtered to smooth the spike trains and obtain the modulating signal S (i.e., motor intent). FIG. 10B shows a schematic of multiple SCDs followed by a demixer. FIG. 10C shows a plot of actual motor intent (red) and decoded motor intent (blue) for an input signal with a single motor intent. FIG. 10D shows a plot of demixing of two overlapped motor intents. Red represents actual motor intents, and blue represents estimated motor intent signals after demixing.

Signals recorded from peripheral nerves may provide an effective and reliable means of controlling powered prosthetic limbs. Longitudinal intrafascicular electrodes (LIFEs) have been used to record extracellular motor activity from peripheral nerves in upper-limb amputees for periods up to several weeks, and the ability to decode the activity and use it for single degree-of-freedom (DOF) control of a prosthetic arm has been demonstrated [4]. However, simultaneous control of multiple DOFs of the prosthesis, which is important for many daily tasks, presents additional challenges. A platform has been developed to simulate recording of extracellular motor activity from multiple LIFE electrodes [5]. An online decoding algorithm that utilizes these simulated recordings has also been designed. FIGS. 10A and 10B show a schematic of the decoder structure. The decoder can include multiple SCDs and a demixer. The SCD decodes motor intent from a LIFE recording. It can include a bandpass filter to attenuate noise and sharpen spikes, a clipping function to identify spikes, and a half-Gaussian smoothing kernel to get a smoothed real-time estimate of motor intent. The demixer can identify the motor intent signals as corresponding to a particular motion class. The demixer requires a learning stage, where recordings from LIFEs can be correlated to motion classes. An simple batched LMS algorithm can be used to train the parameters of the demixer. FIG. 10C shows a plot of a single channel decoding of a sinusoidal motor intent. FIG. 10D shows a plot of demixing of two overlapped motor intents recorded by two LIFEs: the first electrode records activity from the two motor pools while the second electrode records activity from only one (not shown). During the learning stage, the demixer learns to account for common motor intent and provide good estimates of the two different motor intent signals. The decoder can be readily implemented in a real-time, portable, low-power configuration to translate multiple LIFE recordings to motor intent signals that enables multi-DOF control of a powered prosthesis.

While decoded peripheral neural activity recorded by a LIFEs from amputees can be used to control a single degree-of-freedom (DOF) robot arm, existing systems do not allow for recording and decoding of signals from multiple LIFEs for multi-DOF motor control. Embodiments of the subject invention include online decoding algorithms for this task. Embodiments translate motor intent signals to simulated neural recordings from many LIFEs. Motor intent signals drive a pool of simulated motor neurons with various spike shapes, recruitment characteristics, and firing rate properties. Each LIFE records a weighted sum of a subset of simulated motor neuron activity patterns. Simple decoding schemes, such as spike counting, can be an accurate estimator of motor intents using systems and methods of the subject invention.

FIG. 11A shows a schematic of a simulator design. A motor pool generation unit can include response curves of motor neurons mapping input motor intent to frequency of firing, a list of spike templates, and a method to create an array of motor neurons organized into motor pools. FIG. 11B shows transforming motor intent signals to motor neuron firing, and FIG. 11C shows combining neural activity from motor pools into LIFEs recordings.

Figure 12:
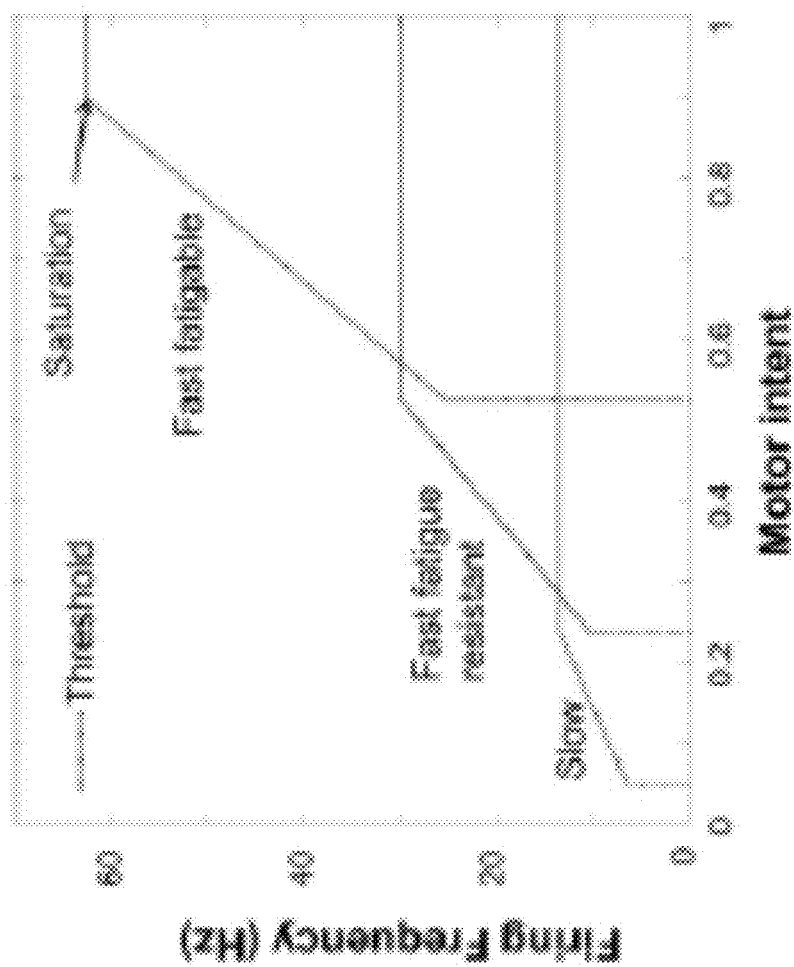
FIG. 12 shows a plot of response curves of motor neurons.

FIG. 12 shows a plot of response curves of motor neurons. The plot shows motor intent on a scale of 0 to 1 (0=no motor intent, 1=maximum motor intent) vs. firing rate of neurons. Saturation is the maximum degree of motor intent at which the firing rate no longer increases, and threshold point is the minimum motor intent to initiate a minimal firing rate.

FIG. 13A shows a schematic of a LIFE SCD. Neural signals and/or muscle signals are bandpass filtered, clipped to remove any residual background noise and normalize spike amplitudes, and filtered by a moving window averager to smooth the spike trains and obtain the modulating signal S (i.e. motor intent). FIG. 13B shows a schematic of multiple SCDs followed by a demixer.

Figure 14:
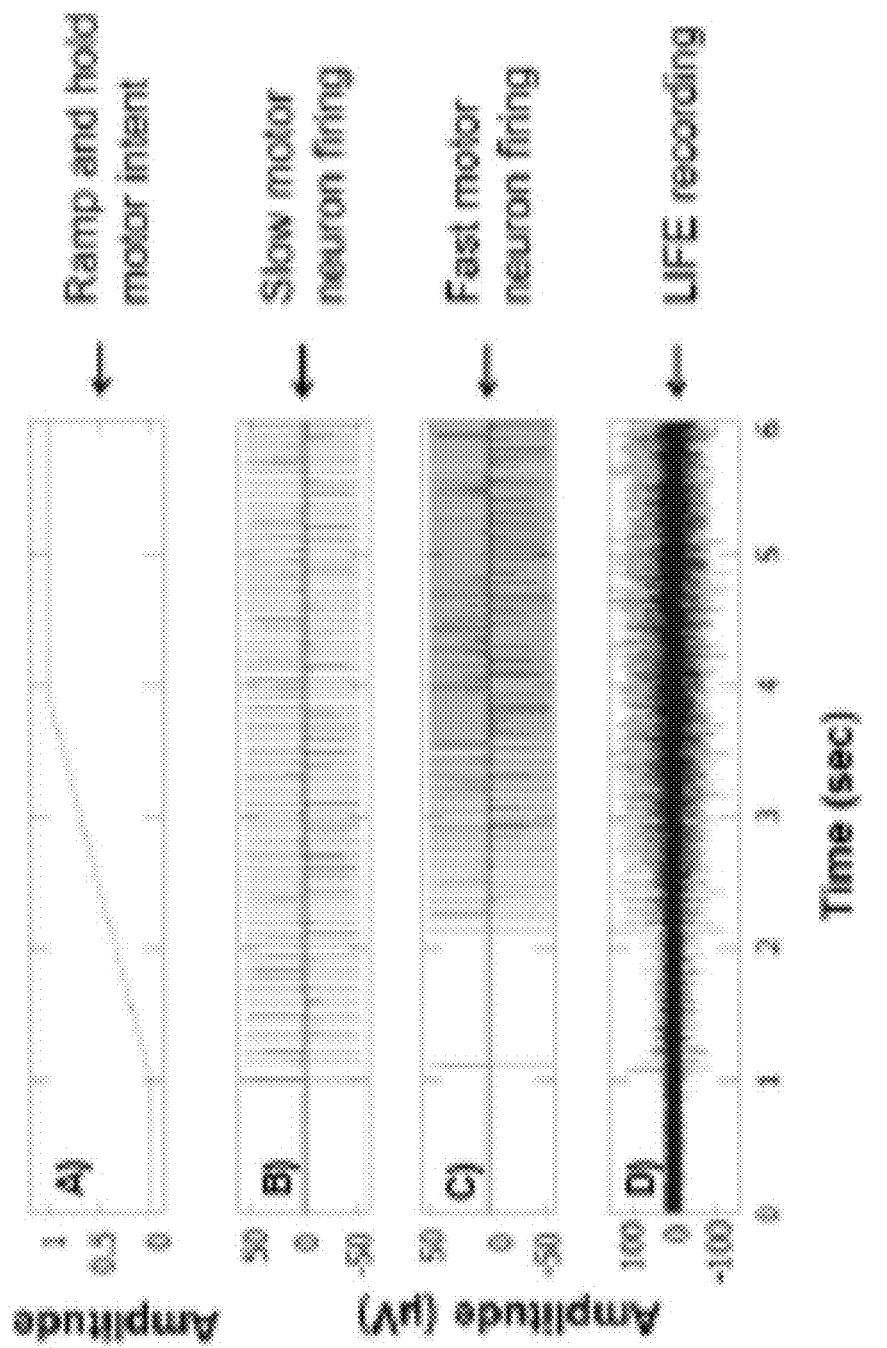
FIG. 14 shows plots of simulated electrode recordings.

FIG. 14 shows plots of simulated LIFE recordings for single DOF tasks. FIG. 14A shows motor intent signal with a steady increase to saturation, and FIG. 14B shows firing of a slow motor unit. FIG. 14C shows firing of a fast motor unit, and FIG. 14D shows a firing pattern recorded by a LIFE electrode.

Figure 15:
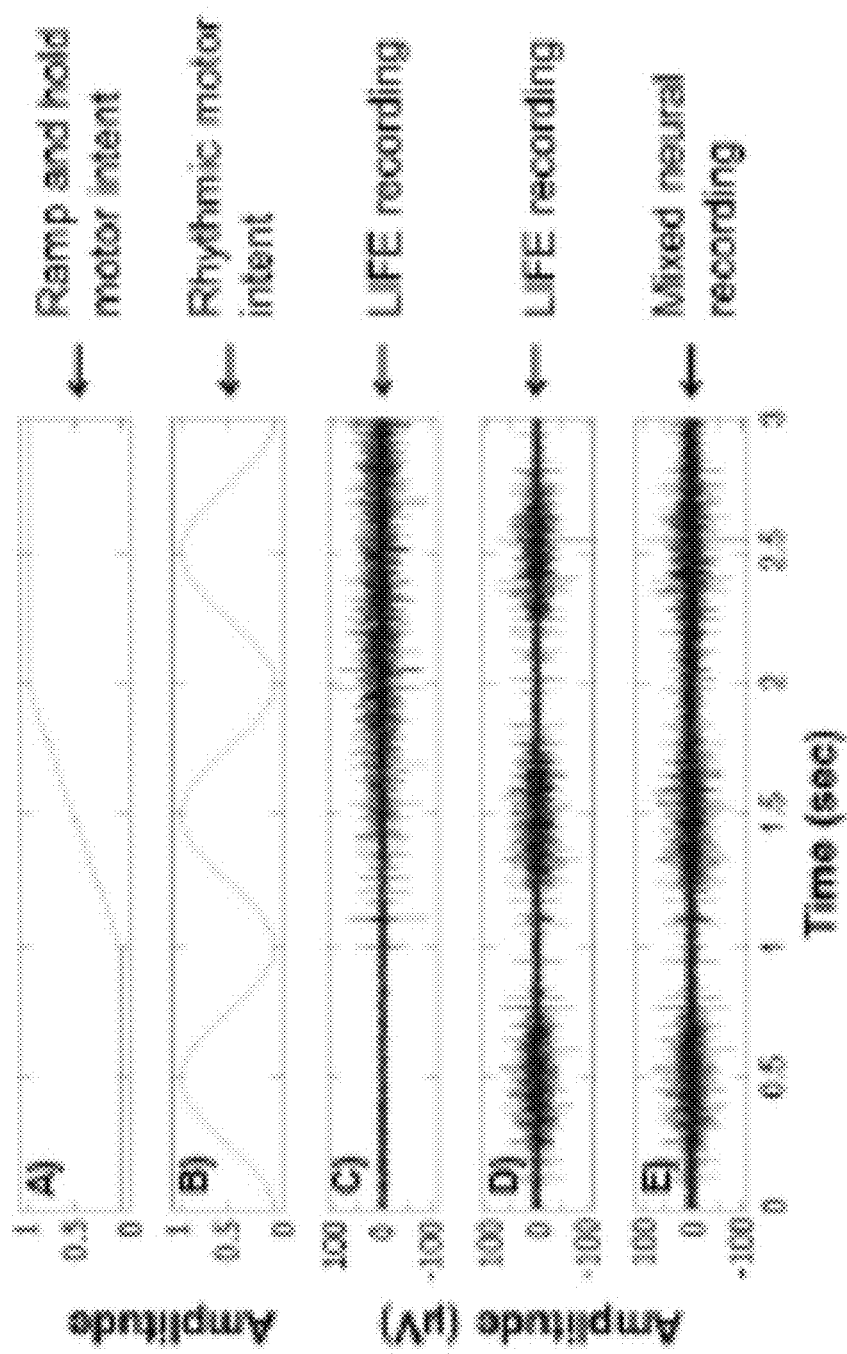
FIG. 15 shows plots of simulated electrode recordings.

FIG. 15 shows plots of simulated LIFE recordings for a multi-DOF task. FIGS. 15A and 15B show two distinct motor intents. FIGS. 15C and 15D show LIFE recordings associated with FIGS. 15A and 15B, respectively. FIG. 15E shows LIFE recordings of mixed neural activity capturing combination of motor intents from FIGS. 15A and 15B for the multi-DOF task.

Figure 16:
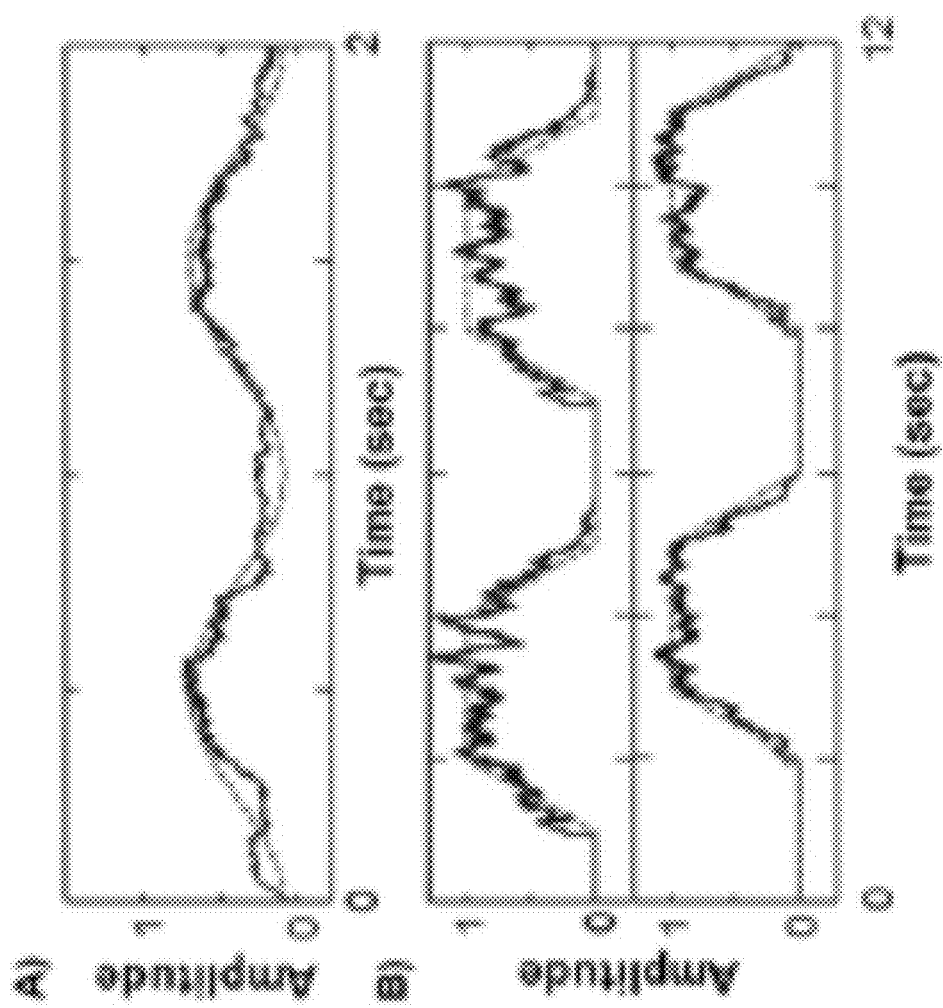
FIG. 16 shows plots of decoding.

FIG. 16 shows plots of decoding. FIG. 16A shows single channel decoding of a motor intent signal. Actual motor intent is represented in red, and decoded motor intent is represented in blue. FIG. 16B shows demixed motor intents. Red represents actual motor intents, and blue represents demixed signals for two motor intents input signals.

Figure 11:
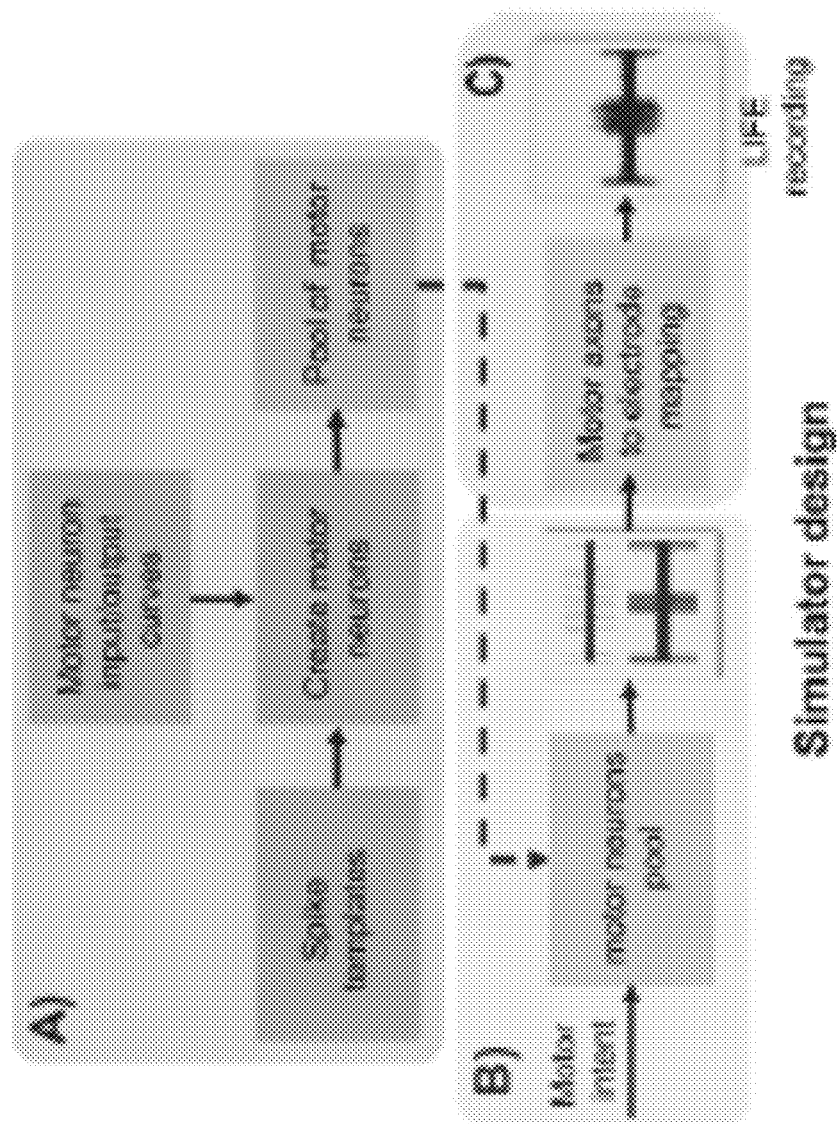
FIG. 11 shows a schematic of a simulator design according to an embodiment of the subject invention.

Motor system organization was taken into account in the design of the simulator shown in FIG. 11. Spinal motor neurons are organized in motor pools, and individual muscles are innervated by a single motor pool. In the peripheral nerves there is some degree of somatotopic organization at the fascicular and subfascicular levels [6]. That is, axons from one motor pool tend to travel together. On initiating an intended movement, the motor neuron axons generate action potentials with different rates of firing to recruit muscles. LIFEs record action potentials from one or more axons as extracellular spikes. Each spike has a characteristic shape.

In an embodiment, LIFEs can be inserted longitudinally into fascicles. This increases the likelihood that an electrode will reside between motor axons of the same motor pool. For decoding motor intent, this would be the optimal placement. However, a LIFE could lie adjacent to axons of two distinct motor pools within a fascicle, which would lead to cross-talk between distinct motor intent signals.

From knowledge of neural control of movement, organization of spinal cord motor neurons and factors influencing recording with LIFEs, the simulator of FIG. 11 was developed. The simulator includes a motor pool generating unit (FIG. 11A) responsible for generating motor neurons and organizing them into motor pools where each motor neuron is characterized by a response curve (FIG. 12) that maps input motor intent signals to output neural firing frequency, a characteristic spike shape and an inter-spike interval distribution. Each motor pool receives one motor intent signal. Neurons in that motor pool convert the motor intent to neural firing (FIG. 11B); the generated LIFEs signal units (FIG. 11C) combine activity from multiple axons to generate activity recorded by many LIFEs.

Figure 13:
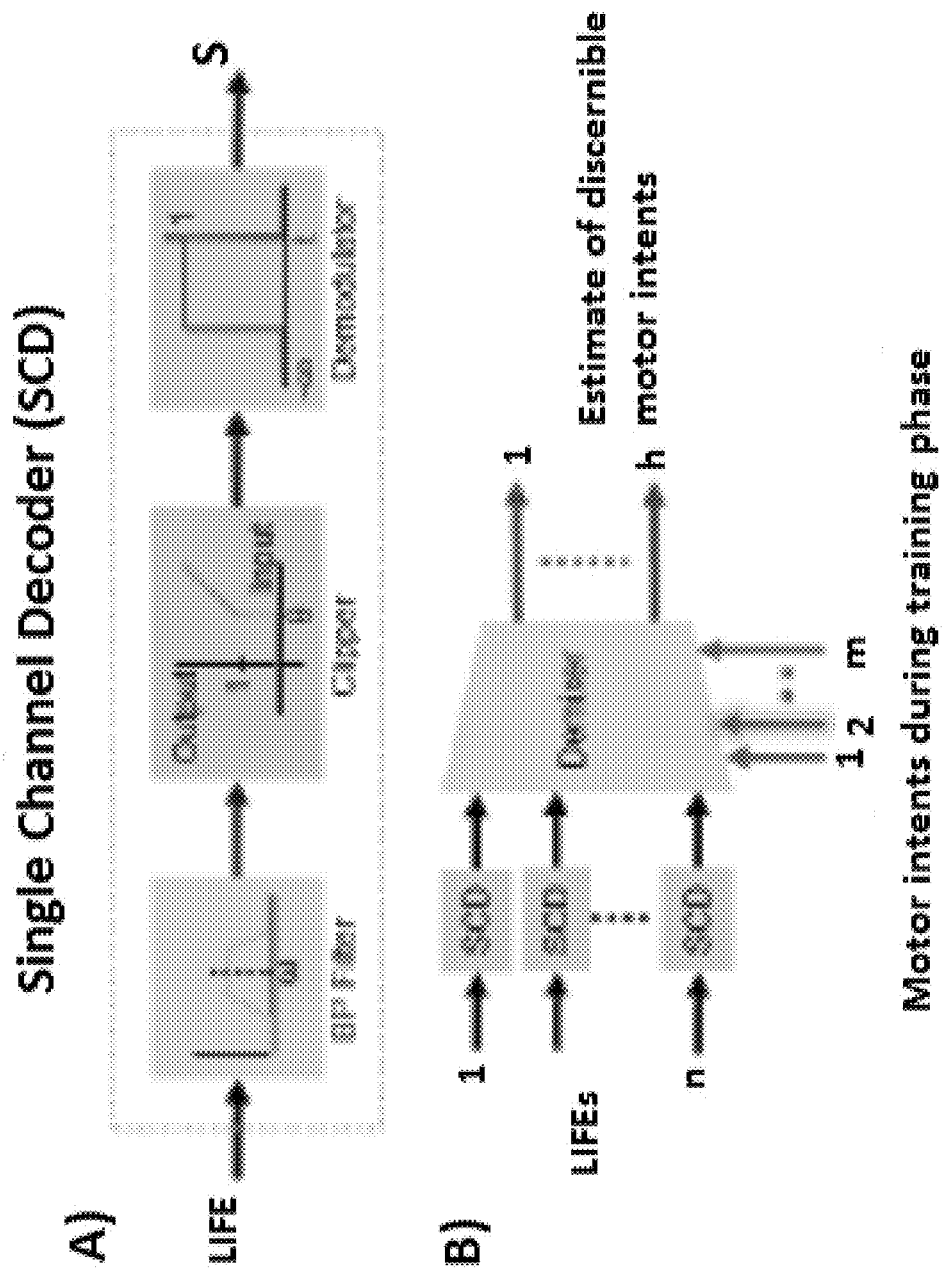
FIG. 13A shows a schematic of an SCD according to an embodiment of the subject invention.
FIG. 13B shows a schematic of multiple SCDs and by a demixer according to an embodiment of the subject invention.

FIG. 13 shows the schematic of a decoder structure according to an embodiment of the subject invention. The decoder can include multiple SCDs and, optionally, a demixer. The SCD can decode motor intent from a LIFE recording. It can include a bandpass filter to attenuate noise and sharpen spikes, a clipping function to detect spikes, and a demodulator to get a smoothed real-time estimate of motor intent. The demixer can identify the motor intent signals as corresponding to a particular motion class. The demixer requires a learning stage, where recordings from LIFEs can be correlated to motion classes.

FIG. 14 shows simulated neurons and a LIFE recording for a single DOF task, ramping up contraction of a muscle to its maximum. Different subsets of motor neurons can differ in firing pattern and spike shape. Neurons with "slow" activity have sparse firing, longer spike duration, and smaller amplitudes. "Fast" neurons have larger amplitudes, shorter spikes, and denser firing patterns. FIG. 15 is a simulation of a multiple DOF task, for example, rhythmically tapping a finger while the wrist is abducted. This simulation shows three types of LIFE recordings that could be obtained during this task.

FIG. 16A displays the result of a single channel decoding of a sinusoidal motor intent. FIG. 16B shows the result of demixing of two motor intents recorded by two LIFEs. The decoder developed here could be readily implemented in a real-time, portable, low-power configuration to translate of multiple LIFE recordings to motor intent signals that enables multi-DOF control of a powered prosthesis.

Embodiments of the subject invention enhance the level of function provided by prosthetic limbs to amputees by providing systems and methods that enable control of advanced prostheses with recorded neural signals and/or muscle signals. Commercially available prostheses use electromyogram (EMG) signals recorded from muscles in the residual limb that are processed to infer motor intent of the user for control. The processing typically includes filtering of EMG signals to eliminate noise and crosstalk, followed by rectifying and then lowpass filtering the signal to obtain a signal to derive the prosthesis. In ongoing research and development efforts other biological signals such as electroencephalograms (EEG) or neural signals and/or muscle signals detected by cortical and peripheral interfaces are being used for prosthetic control. A wide variety of decoding algorithms can be used to enable the use of such signals. The decoding algorithms differ depending on the types of biological signals recorded, the design and properties of machine-tissue interfaces, the design and function of prostheses, and the extent of injury.

Figure 17:
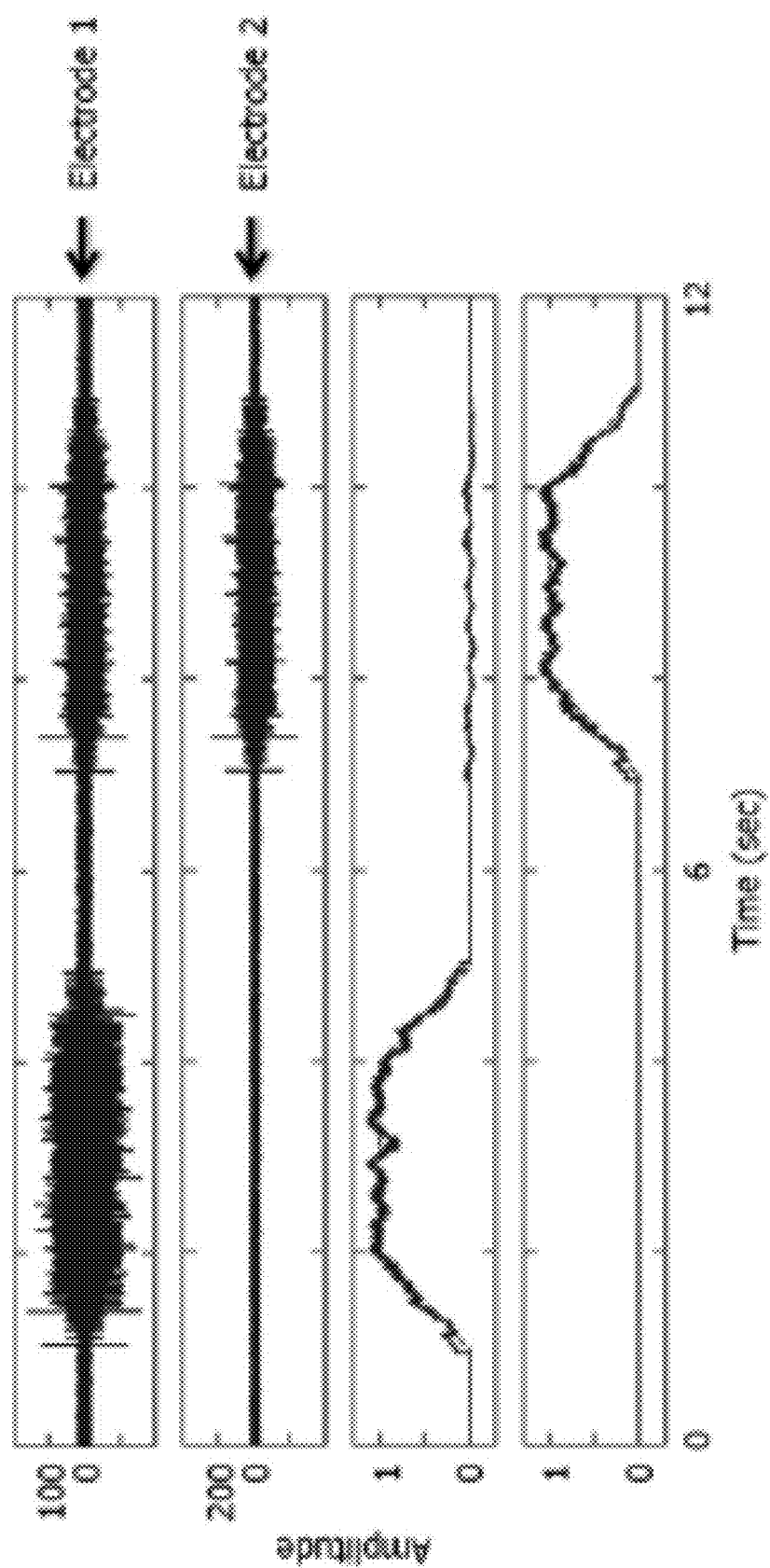
FIG. 17 shows plots of two electrodes.

FIG. 17 shows traces of two electrodes, actual (red) and estimated motor intent (blue) during the training phase of the demixer according to an embodiment of the subject invention. Referring to FIG. 17, it was assumed that two motor intent signals activate two motor pools which are subsequently recorded by two LIFEs. The first LIFE records activity from both motor pools while the other electrode records activity from only one. The training phase requires activation of one motor pool at a time by selecting non-overlapping motor intents. After the demixer has been trained on these well-defined datasets then it is able to decode different patterns of motor intents (FIG. 10D).

FIG. 3 is a diagram of a simulator design for neural interface recording electrodes. Referring to FIG. 3, u is motor intent vector. G transforms motor intent u to activation state of motor neurons x. The function μ converts activation state vector x to neural firings. H is the recording electrode function; it maps neural firing to electrode recordings. W is ambient noise. The panel "an element of the vector μ" describes how a neuron activation state is transformed to neural firing rates. The panel "making of spike templates" describes the process of constructing motor neurons spike templates which depends on many factors such as axon myelination and electrode distance, shape and placement. (Simulator disclosed in U.S. Provisional Patent Application Ser. No. 61/714,578).

Figure 5:
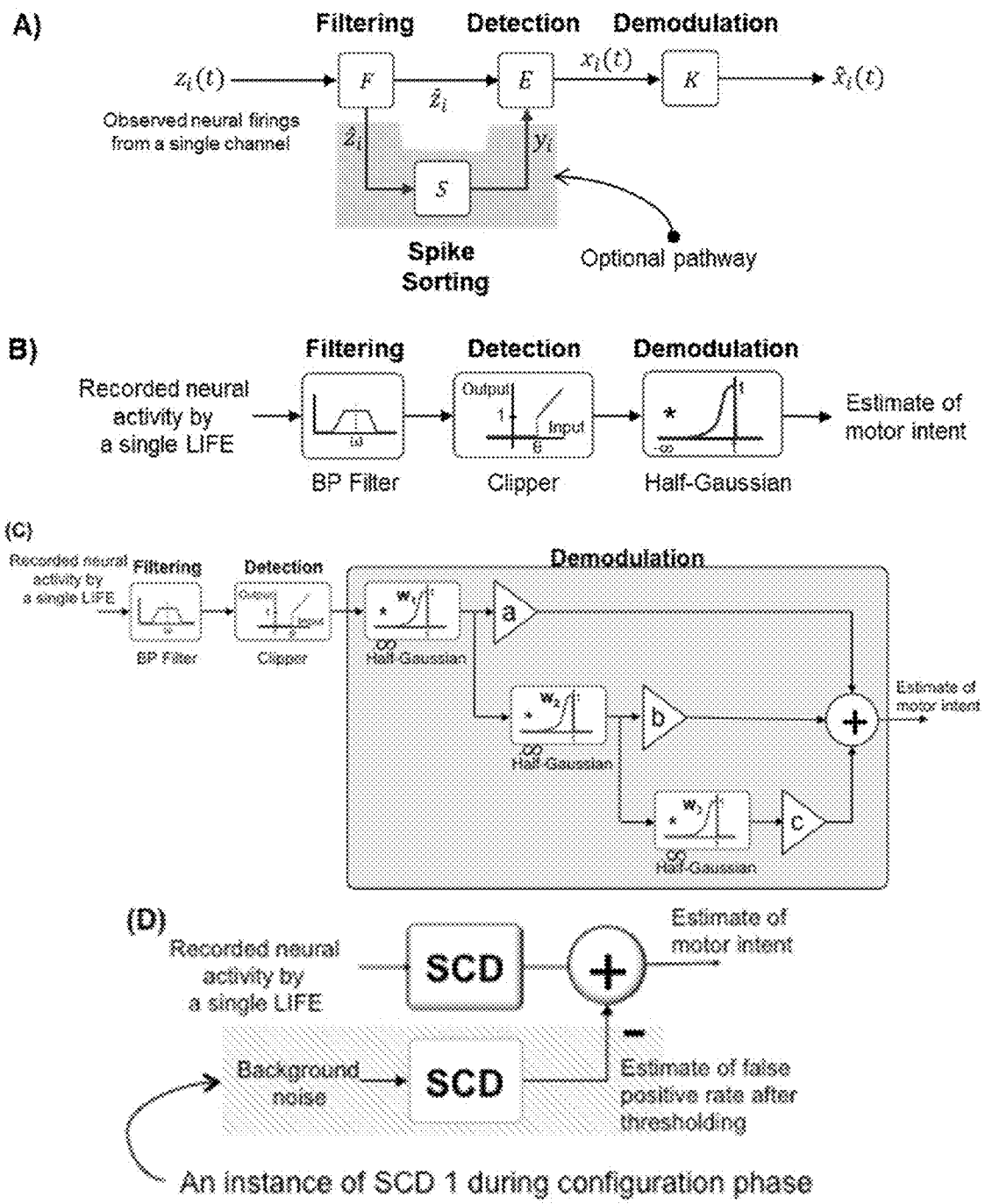
FIG. 5A shows a diagram of a single channel decoder (SCD) design according to an embodiment of the subject invention in which a spike sorting algorithm is used as part of the SCD.
FIG. 5B shows a diagram of an embodiment of the SCD that includes a bandpass filter, a clipping function for detection, and a half-Gaussian function for demodulation.
FIG. 5C shows a diagram of an embodiment of the SCD that uses a cascade of filters in the demodulation stage.
FIG. 5D shows a diagram of an embodiment of the SCD that uses an estimate of the false positive rate to improve the quality of the detection algorithm.

FIG. 5 is a diagram of an SCD design, subunits, and function. FIG. 5A shows the general single channel neural decoder design. It includes: a filter F to attenuate noise and sharpen spikes; a detector E to identify spikes time and amplitude and reshape spikes to enhance performance of the demodulation stage; and a demodulator K to recover intended motor commands from neural firings. The optional pathway (greyed region in A) is for spike sorting. Spike sorting decomposes the single channel neural recording $z_i$ based on identifiable spike shapes to a vector $y_i$ of separated spike trains. $z_i(t)$ is recording from a single electrode. z-hat$_i(t)$ is filtered neural recording. $x_i(t)$ is possibly a vector of identified spikes, and x-hat$_i(t)$ is recovered motor intent signal(s). FIG. 5B shows an example of a LIFE single channel decoder (LSCD): neural signals and/or muscle signals are bandpass filtered, clipped to remove any residual background noise and normalize spike amplitudes, and demodulated by a Half-Gaussian smoothing kernel to get a smoothed real-time estimate of motor intent.

Figure 6:
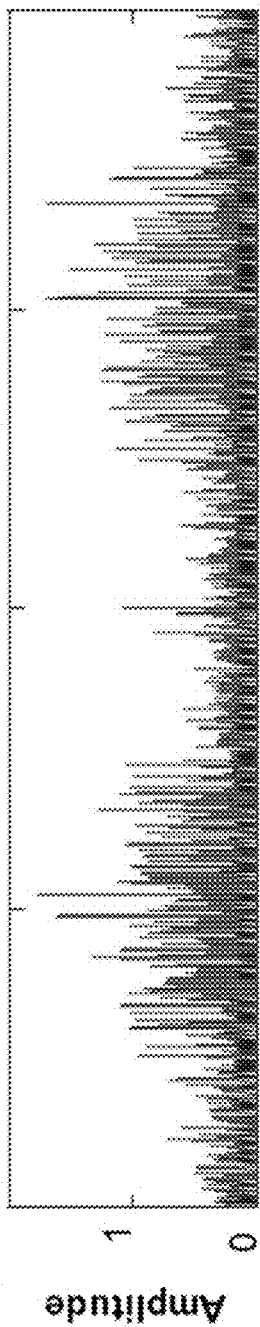
FIG. 6 shows plots of decoding.
Figure 6:
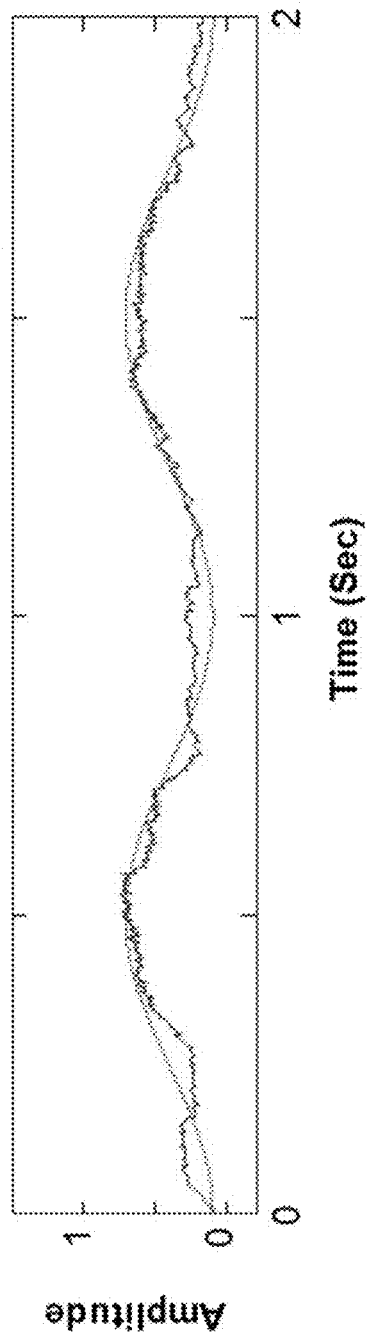

FIG. 6 shows results of decoding with a Half-Gaussian demodulator. FIG. 6A shows spike trains from a single simulated recording of a LIFE electrode after being clipped and renormalized, and FIG. 6B shows actual motor intent (red dashed trace) versus Half-Gaussian filtered motor intent (blue trace).

Figure 7:
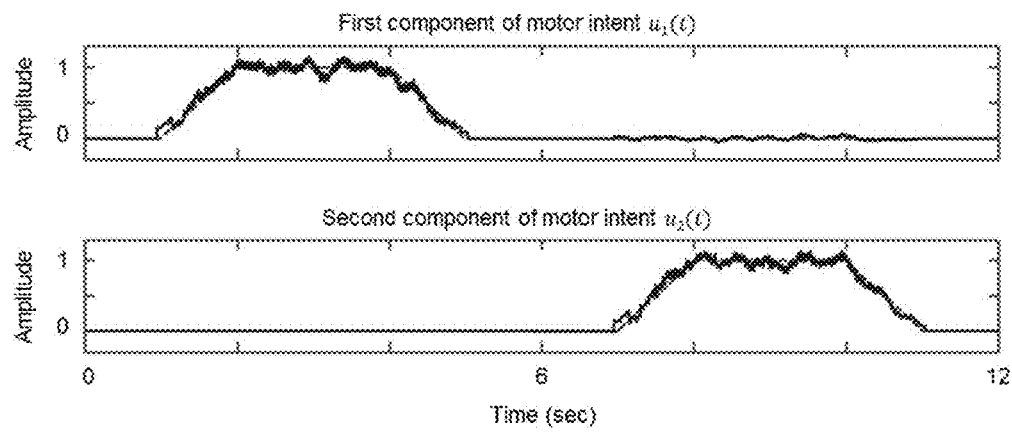
FIG. 7 shows plots of orthogonal motor intent signals and their estimates after learning.
Figure 7:
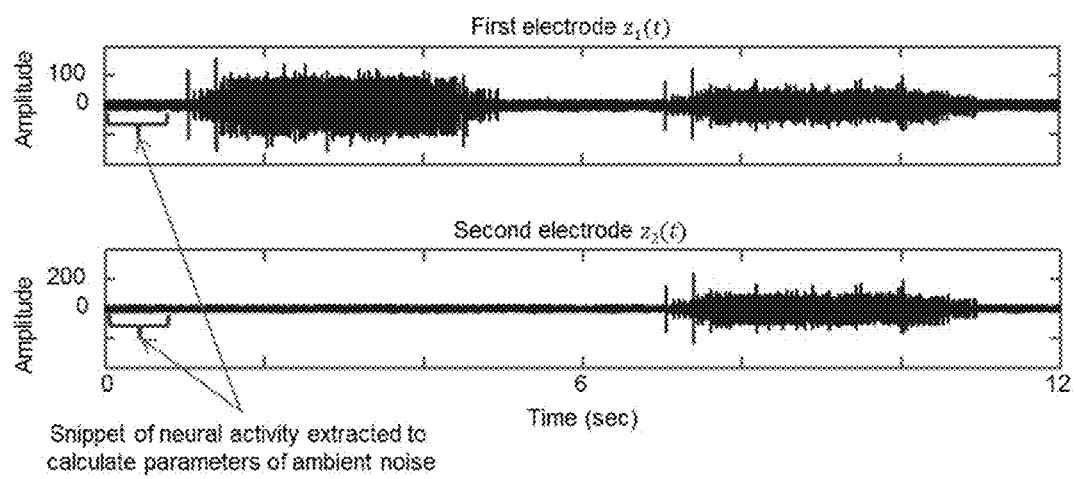

FIGS. 7A and 7B show examples of orthogonal motor intent signals and their estimates after learning. During the configuration phase, the configuration unit cycles over a set of orthogonal components of the motor intent vector (red dashed traces) and calculates parameters of ambient noise and trains the demixer. Blue traces are the output of the demixer after training is complete. The demixer identifies the motor intent signals as corresponding to a particular motion class. The demixer requires a learning stage, where recordings from electrodes are correlated to motion classes. A gradient descent algorithm or a similar form of adaptive algorithm can be used to train the parameters of the demixer.

Figure 8:
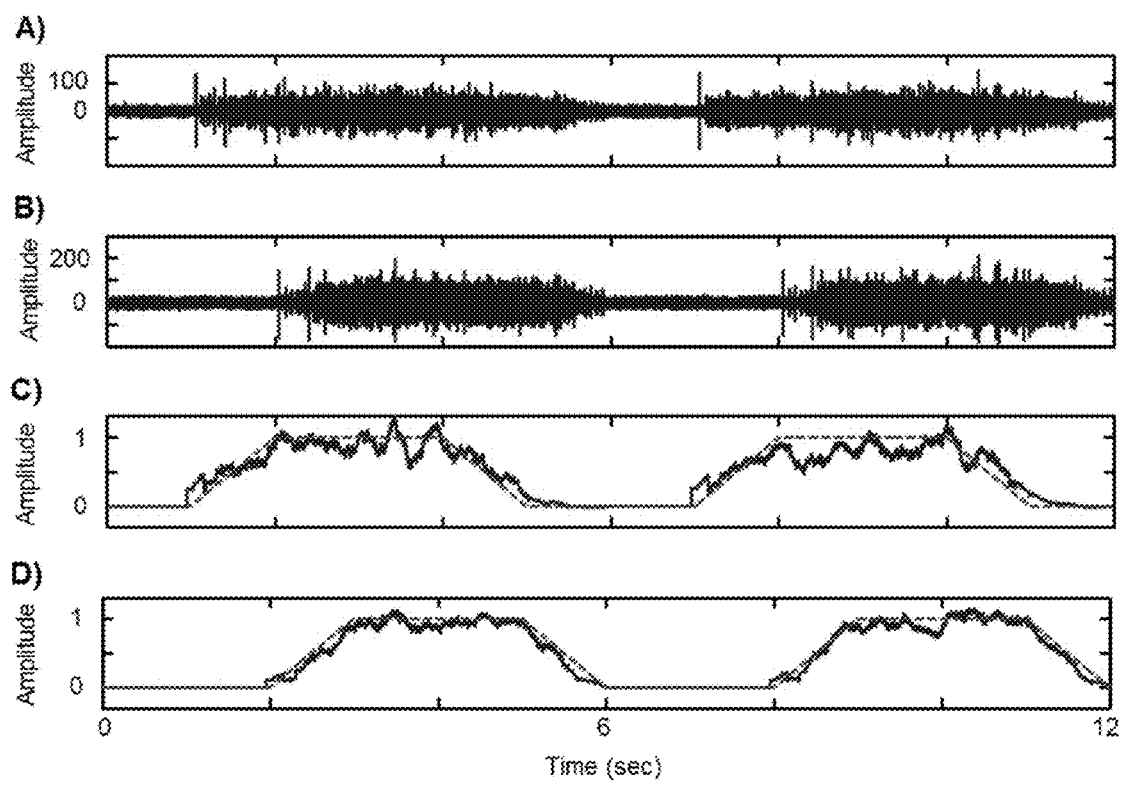
FIG. 8 shows plots of demixing of two overlapped motor intents.

FIG. 8 shows results of demixing of two overlapped motor intents recorded by two LIFEs: the first electrode (FIG. 8A) records activity from the two motor pools while the second electrode (FIG. 8B) records activity from only one. During the learning stage, the demixer learns to account for common motor intent and provide good estimates of the two different motor intent signals—FIG. 8C and FIG. 8D. In FIGS. 8C and 8D, actual motor intents are represented in red and estimated motor intent signals after demixing are represented in blue.

Referring again to FIG. 3, the simulator can include the following units: motor intent generation unit that generates multiple motor intents with different shapes—rhythmic, ramp-up, etc.; motor pool construction unit that generates multiple motor neurons with different spike shapes and response characteristics; and electrode function unit that defines the electrode recording process. With the simulator, realistic LIFEs recording data can be simulated, as well as different combinations of motor pool involvement, different spike morphologies, and special effects such as superposition of spikes.

Figure 4:
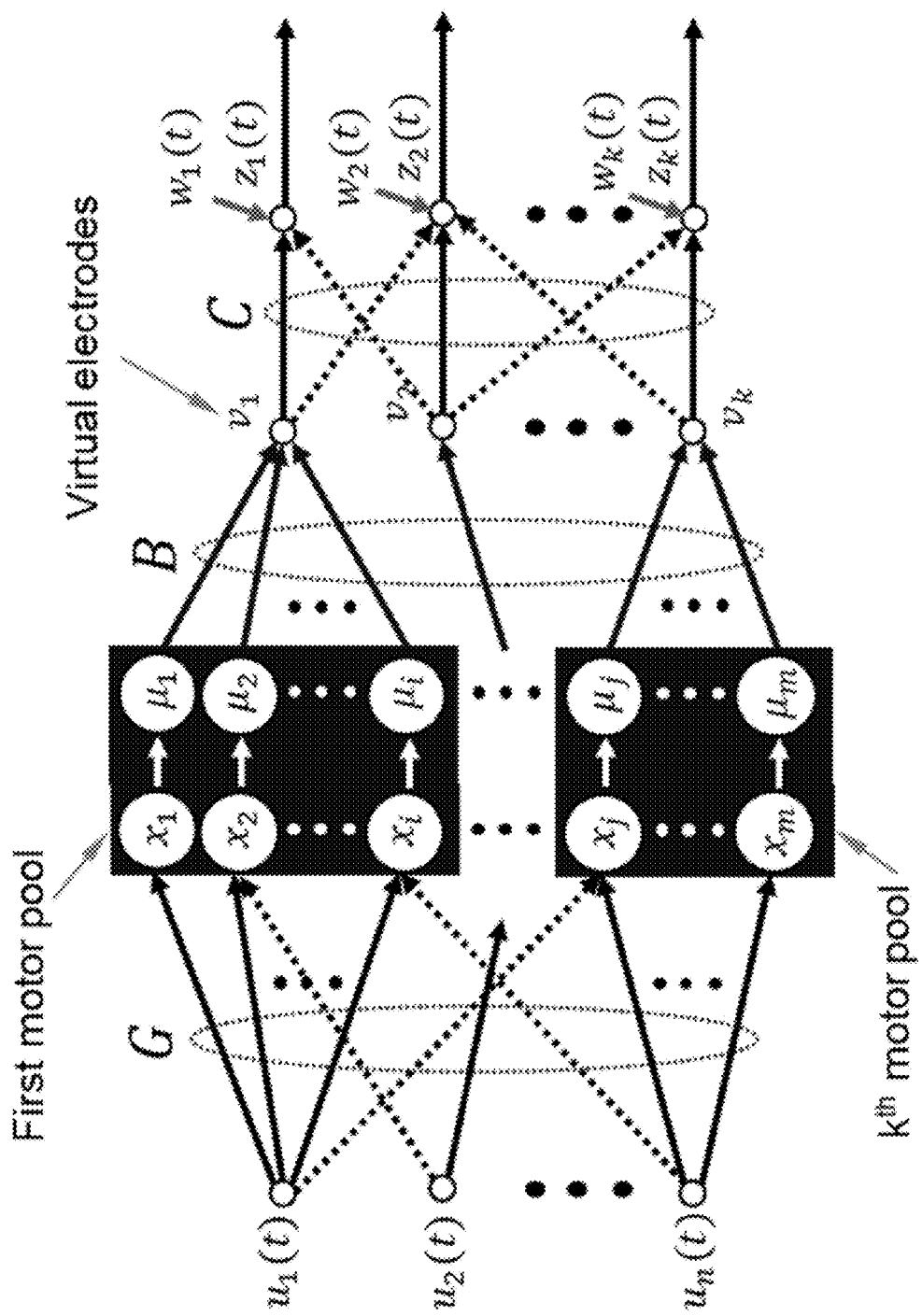
FIG. 4 shows a diagram of a computational and simulation model according to an embodiment of the subject invention.

For the simulation of multiple LIFEs, some of the elements of the simulator were specialized, specifically the electrode function unit. FIG. 4 shows a computational and simulation model for recoding with LIFEs. Referring to FIG. 4, n motor intent signals are transformed via G to m motor neuron neural firings. These motor neurons are organized into k motor pools. The matrix BC describes how neural activity from different motor pools sums to produce LIFE recordings. Suppose recoding is from k electrodes $\{z_i(t), i=1 \ldots k\}$, then in principle activity can be detected from at most k motor pools. Let u(t) be a vector of n, n≥k, motor intent signals activating spinal cord motor neurons $x_i$'s. G is the connectivity matrix that maps u to motor neurons x organized in motor pools. The dashed arrows between u and x represent the situation that a motor intent can affect multiple motor pools. The functions $\mu_i s$ transform motor intent signals to neural firings with various spike shapes, recruitment characteristics, and firing frequencies.

Peripheral nerves are somatotopically organized at fascicular and subfascicular levels. That is, axons from one motor pool tend to travel together. Then, the vector v will represent the optimal placement of a LIFE electrode within a group of axons stemming from one motor pool. v is called virtual electrodes. The matrix B is the contribution of each neuron in a given motor pool to the signal of a virtual LIFE. The matrix C is the cross-talk (i.e., common motor intent signal across multiple LIFEs) matrix in case of a less than ideal placement of LIFEs. The dashed arrows in FIG. 4 represent cross-talk between different motor pools. The LIFE recording model can be described by the following equation:

$$z(t) = Cv(t) + W(t), \quad (1)$$
$$= CB\mu(Gu(t)) + W(t),$$

where the vector W(t) is ambient noise. The matrix CB is not known a priori.

From knowledge of z(t) the matrix CB, the matrix G, and the motor intent vector u(t) must be estimated. This is a nonlinear estimation problem, and the optimal filter is hard to compute so approximation techniques can be used. FIG. 5B show the schematic of the LIFEs decoder structure. The decoder includes multiple SCDs and, optionally, a demixer. The SCD decodes motor intent from a LIFE recording. It includes a single band-pass Gaussian shaped filter, a clipper, and a demodulator. The bandpass filter bandwidth is proportional to the inverse of the average width recorded spikes. Spikes width information must be known a priori from pervious neural recordings. Even then, the bandwidth parameter can be tuned during operation of the decoder for better results. The clipping function is described by the following equation:

$$Clip(x; \theta) = \begin{cases} \frac{x}{\theta}, & x \geq \theta \\ 0, & \text{otherwise} \end{cases} \quad (2)$$

where $\theta$ is the threshold parameter calculated during the configuration phase of the decoder from quiescent neural recordings. The bandpass filter together with the clipper eliminates much of the ambient noise W(t), reducing equation (1) to CBµ(Gu(t)). The demodulator transforms CBµ (Gu(t)) to CBGu(t), effectively eliminating the nonlinear function µ. The demodulator is implemented using a Half-Guassian smoothing kernel. The standard deviation of the kernel is known as the kernel time constant. The time constant can be set such that a spike of 2 milliseconds (ms) in width produces an output with a 250-ms standard deviation. The Half-Gaussian is implemented using FIR filter. The number of samples in the filter can be set to be 4 times the filter time constant. FIG. 6 shows the result of a single channel decoding with Half-Gaussian.

FIG. 5C shows another example of a more elaborate single channel LIFE decoder. In this embodiment, the neural signal and/or muscle signal is bandpass filtered, clipped to remove any residual background noise, and normalized to standardize spike amplitudes. Then, the signal is demodulated by a cascade of Half-Gaussian (HG) smoothing kernels to obtain a better smoothed real-time estimate of motor intent. The constants (a, b, and c) scale the amplitude of the output signals in each branch while the widths of the HG kernels ($w_1$, $w_2$, and $w_3$) affect the temporal characteristic of the signals. The widths and constants are set in a manner that satisfies different requirements for the response speed of the demodulator and the smoothness of its output. The cascading of kernels can include two or more stages and can include kernels other than Half-Gaussian kernels, such as square, triangle, or any other filtering window shape.

During the decoding process, false detection of spiking activity could lead to an overestimate of the amplitude of motor intent. FIG. 5D shows a method for reducing the detrimental effects of false detection on estimates of motor intent. During the configuration phase, recording channel threshold parameters ($\theta$) are determined and set in the SCDs. Also, an estimate of false positive rate can be calculated by processing background noise with SCDs after setting the threshold parameter during the configuration phase. The estimates of false positive rates can be used to reduce the effects of the false positive rate during recording and decoding of input signals.

Finally, the demixer's job is to estimate the various components of motor intent from CBGu(t) data. This operation requires an estimate of the CBG matrix. For this, the demixer uses a learning phase, where recordings from LIFEs are correlated to intended actions, as shown in FIGS. 7A and 7B. During the configuration phase, the configuration unit cycles over a set of non-overlapping motor intent signals (as shown in FIG. 7A) and calculates parameters of ambient noise and trains the demixer. In this case, a simple batched LMS algorithm was used to train the parameters of the demixer. FIGS. 8C and 8D show results of demixing of two overlapped motor intents recorded by two LIFEs: the first electrode records activity from the two motor pools (FIG. 8A) while the second electrode records activity from only one (FIG. 8B).

In an embodiment, an MCD can include SCDs, a demixer, and a configuration unit. In general, the SCD can include a bank of bandpass filters (BBP), a detector, and demodulators. The demixer is an adaptive filter that minimizes error between output estimates and motor intent. The configuration unit performs initialization and parameter estimation and trains the demixer during the configuration phase.

Several methods for filtering with a bank of band pass filters exist with varying levels of performance. The idea is to decompose the signal into sub-bands and filter the resulting signal in the sub-band then recomposing the signal to obtain a filtered output. An example of this is the method of wavelet de-noising commonly used in filtering of neural recordings.

In one embodiment, the decoder uses a set of three FIR filters whose parameters are set based on sampled Symlet 7 wavelets. The de-noising can be done using soft thresholding based on noise parameters calculated during the configuration phase of the decoder. The threshold can be set to the scaled maximum of the standard deviation and kurtosis of background noise. The background noise tends to be 1/f noise with a Gaussian distribution of its amplitudes. However, in certain cases when the background activity is the sum of many distant firings of many neurons, the kurtosis of the background noise becomes the determining factor in effective de-noising. Other de-noising procedures are possible, for example a Weiner and Kalman filter combined with wavelet de-noising have been reported in literature.

The most common spike detectors are the comparator and the Schmitt trigger. These detectors are used to find the time of spike occurrence. Inter-spike intervals and instantaneous frequency can be calculated using spike timing events. An alternative method is to count the number of spikes in bins of fixed width. It has been argued that spike counting and instantaneous frequency may be sufficient for determining the level activity of a neuron, and that not much information may be contained in the duration and amplitude of the spike.

If a twitch fiber response to action potentials is considered, it can be seen that spike shapes and duration matter. Different types of spikes result in different twitch responses that are variable in amplitude and duration. Also, action potential of different sizes and duration cause varied levels of graded potential on postsynaptic cells. As a result, the variability of graded potential duration, amplitude, and shape alter the characteristic of fringing postsynaptic cells. Furthermore, for some neural recording interfaces superposition of spikes creates spikes of large amplitude. These spikes could have been from to the same muscle or a sum on distant neurons. Their added effect matters in biology and should therefore matter in neural decoding. The information contained in spike amplitudes and duration is essential for accurate decoding.

Essentially, few methods have been reported in literature that consider the amplitude of biological signals and duration in motor decoding. Two methods were developed initially for EMG analysis. These methods are full-wave rectification and root mean square. It has been shown that full wave rectification coupled with nonlinear energy operator (NEO) has the best performance in terms of low false positive detection. Concerns with these two methods include: full wave rectification and squaring tend to increase the mean and variance of the back ground noise, which might require increasing the threshold, and increasing the threshold might increase true negative errors; and full wave rectification doubles the frequency content of the detected signal while RMS doubles amplitudes and frequencies of the recorded signals—this effect alters non-stationary signal characteristics of the estimated motor intent signals.

Therefore, instead of using full-wave rectification or squaring of signals, nonlinear reshaping functions of the subject invention can be used that are a modification of thresholding functions used in wavelet de-noising. Two examples of these function are given. The normalization clipper described by Equation 2 above and spike taming function:

$$Tame(x;\theta) = \begin{cases} \dfrac{\left(\frac{x}{\theta}\right)^n}{1+\left(\frac{x}{\theta}\right)^d} & x \geq \theta \\ 0, & \text{otherwise} \end{cases} \quad (3)$$

The tame function for $n=d+0.5$ for $d>1$ tends to suppress amplitudes less than 0 and decrease excessively large amplitudes.

Demodulators are essentially smoothing kernel estimators. Kernel filters can be implemented using FIR filters. The parameters of the kernel can be specified in a way to perform the desired demodulation of spike firings to obtain a smoothed estimate of motor intent. The shape of the kernel determines whether the kernel functions as a low pass of high pass filter. Most demodulators are low pass filters. Kernels with positive parameters are lowpass filters. The degree of smoothing depends on the time constant of the filter and the shape of the kernel. Kernels that exhibit discontinuity tend to produce jagged estimates. Kernels with large time constants produce smooth estimates but at the cost of large bias. The Gaussian kernel is an example of a smoothing kernel commonly used to estimate non-stationary Poisson process parameters. Unfortunately, the filter is non-causal. The truncated version of the filter has a delay equal to the time constant of the filter. To obtain a causal filter we have used the half-Gaussian also known as folded Gaussian function. The time constant of the filter is initialized during the configuration phase of the decoder. Other forms of kernels include but are not limited to the exponential kernel, square, and triangle. The Half-Gaussian kernel is special in the sense that it tends to emphasize immediate spike contribution to history of past spikes.

Simulation showed that non-adaptive Half-Gaussians work reasonably well in estimating motor intent signals. In an embodiment of the subject invention, the Half-Gaussian is further enhanced by making the filter time constant depend on the rate change of motor intent. This effect can be formalized by the following equation:

$$\sigma_i = \gamma \dfrac{d\theta_t}{dt}. \quad (4)$$

$\sigma_i$ must also be bounded between the maximum allowable time constant of 250 ms and minimum of 10 ms.

In an embodiment, a simple linear adaptive filter trained by a batched LMS filter can be used as a demixer. Choice of such a demixer stems from the fast that much of the nonlinear mapping in handled by the SCD and that the demixer's job can be to sort linearly-mixed motor intent classes.

In an embodiment, a method of decoding neural signals and/or muscle signals includes using a system (e.g., a decoder) as described herein to decode the signals.

Embodiments of the subject invention also include fabricating systems as described herein.

Systems and methods of the subject invention have at least the following advantages over existing neural signal and muscle signal devices: simultaneous control of multiple degrees of freedom; graded control of each degree of freedom; decoding of neural data from human as well as animal data; decoding from cortical and peripheral signals recorded by neural interfaces; works with many neural interfaces, including but not limited to cortical arrays, tfLIFE, LIFE, and CUFF; decoding of EMG data derived from electrodes placed in or near the muscle or on the surface of the skin.

In an embodiment, an SCD includes a subunit called a spike-sorting unit. Whether the unit is present or not can depend on the design and function of the recording neural interface and the degree of superposition between neural sources. In some cases, spike sorting is essential and may provide information that can boost the performance of neural decoders. Spike sorting is a collection of methods to provide analysis of neural data. Spike sorting algorithms rely on the fact that neurons communicate using spikes (i.e., pulses of characteristic shape and finite in duration) and that each neuron or subset of neurons has a distinct spike shape. Spike sorting is to distinguish spikes from noise or different spikes from each other and separate these spikes into distinct classes.

Spike sorting is useful in studying brain function and understanding which group of neurons in the brain or peripheral nervous system is doing what. Also, spike sorting can be used in conjunction with a decoding algorithm to provide a higher degree of control of powered prostheses. In general, spike sorting methods require the following steps: acquire raw neural data; filter the neural data to attenuate background noise; detect spikes; alignment of spikes (superimposing the spikes detected to detect special features that would distinguish one spike from another—this is usually done by visual inspection as automated algorithms are still in early stages of development); recognizing the special features; classify the features to verify they are independent; and use the classified features to detect spike shapes.

The decoder of the subject invention can be implemented (stored and programmed) in many different locations, including but not limited to, an external device, a prosthesis, an implanted device, or a CHIP. The decoder unit can be set up in the initialization phase using an experimental protocol typically conducted during the first time the external appliance (e.g., prostheses) is used by the user and/or fitted to the user. This initial setup can be referred to as the initial setup procedure (ISP). In an embodiment, the ISP includes the following steps: users will be implanted with neural interface to record neural signals and/or muscle signals; recorded neural signals and/or muscle signals from the electrodes channels are connected to single channel decoders; users are required to mentally produce (imagine to do a task) well-defined motor intent signals that will actuate the external device in a well-defined manner; users are required to reproduce these mental tasks using their intact embodiment (i.e., physical body) hands and legs, thereby producing a well formed set of motor templates; motor templates are natural intuitive movement patterns corresponding to the motor intent signals that the subject naturally uses to control appliances; motor templates are stored in the configuration unit of the decoder for future tuning of the decoder, if need requires it; and the configuration unit uses the motor templates and the associated neural recording to train the demixer.

In an embodiment, after the ISP is done, the decoder is configured for the first time and is ready for operation. It is possible that after long term use of the prosthesis (appliance) that the response of the prosthesis may not match user intended actions. This could be due to mechanical, electrical, environmental, or biological factors. In this case, the decoder should be tuned to restore its performance. The tuning of the decoder can be done through decoder tuning protocol (DTP). DTP is a set of instructions that the user must follow to tune the prosthesis.

In an embodiment, the DTP includes the following steps: a motor template is visualized or vocalized to the user; the user is required to imagine the task as he/she did in ISP; neural signals and/or muscle signals will be decoded by the decoder and compared to motor templates; the task is repeated until the error between the motor template and intent action is eliminated; and the process is repeated for every motor template. The DTP can be implemented in portable devices (e.g., a laptop) or in the prosthetic arm itself. FIG. 9 shows an example of how to tune a prosthesis by connecting it to a laptop and running the DTP.

The methods and processes described herein can be embodied as code and/or data. The software code and data described herein can be stored on one or more computer readable media, which may include be any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); or other media now known or later developed that is capable of storing computer-readable information/data. Computer-readable media should not be construed or interpreted to include any propagating signals.

The invention includes, but is not limited to, the following embodiments:

Embodiment 1

A system to decode intended motor actions from neural signals and/or muscle signals recorded by multiple neural interface electrodes and/or from EMG signals (e.g., EMG signals recorded by multiple electrodes placed in or near muscles).

Embodiment 2

The system according to embodiment 1, that operates in real-time and is implemented in a portable, low-power configuration.

Embodiment 3

The system according to any of embodiments 1-2, that interprets signals from a single or multiple electrodes to enable single or multiple degree-of-freedom control of a powered prosthesis.

Embodiment 4

The system according to any of embodiments 1-3, in which the intended motor action consists of the intended class of action and the intended degree of action.

Embodiment 5

The system according to any of embodiments 1-4, in which de-noising of the input signals is achieved by a bank of band pass filters that may be tunable and that may use wavelets with several thresholding criteria.

Embodiment 6

The system according to any of embodiments 1-5, in which a nonlinear reshaping function is used to detect spikes, to suppress noise, and/or to normalize spike amplitudes.

Embodiment 7

The system according to any of embodiments 1-6, in which a tunable demodulator is implemented to estimate motor intent signals, wherein the time constant of the demodulator is tuned based on the rate of change of the current estimate of the motor intent.

Embodiment 8

The system according to any of embodiments 1-7, in which an adaptive learning architecture is used to enable the system to automatically learn, in real-time or off-line mode, to decode motor intent from recorded neural signals and/or muscle signals.

Embodiment 9

The system according to any of embodiments 1-8, in which the intended motor action is used to control an external powered appliance such as a single or multiple degree-of-freedom robot.

Embodiment 10

The system according to any of embodiments 1-9, in which the intended motor action is used in an interactive computing environment (e.g., to control an avatar).

Embodiment 11

The system according to any of embodiments 1-10, used to assess muscle activity and neuron function during nerve stimulation and/or regional anesthesia.

Embodiment 12

The system according to any of embodiments 1-11, with one or more single channel decoder that downsamples and compresses the recorded neural signal and/or muscle signals to allow for faster and more efficient transmission from the decoder to the controlled device or interactive computing environment.

Embodiment 13

A system for decoding intended motor actions from neural signals and/or muscle signals recorded by one or more electrodes, wherein the system comprises: at least one single channel decoder (SCD); and a demixer in operable communication with the at least one SCD.

Embodiment 14

A method of decoding intended motor actions from neural signals and/or muscle signals, wherein the method comprises using the system of any of embodiments 1-13 to decode the signals.

All patents, patent applications, provisional applications, and publications referred to or cited herein (including those listed in the References section) are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Wodlinger B, Durand D M: Localization and Recovery of Peripheral Neural Sources With Beamforming Algorithms. IEEE Trans. on Neural Sys. and Rehab. Eng., 2009, October, 17(5):461-8
2. Clark G A, Ledbetter N M, Warren D J, Harrison R R: Recording Sensory and Motor Information from Peripheral Nerves with Utah Slanted Electrode Arrays. 33rd Annual International Conference of the IEEE EMBS Boston, Mass. USA, Aug. 30-Sep. 3, 2011
3. Micera S, Navarro X, Carpaneto J, Citi L, Tonet O, Rossini P M, Carrozza M C, Hoffmann K P, Vivo M, Yoshida K, Dario P: On the Use of Longitudinal Intrafascicular Peripheral Interfaces for the Control of Cybernetic Hand Prostheses in Amputees. IEEE Trans. on Neural Sys. and rehab. Eng., vol. 16, no. 5, October 2008
4. Dhillon G S, Lawrence S M, Hutchinson D T, Horch K W: Residual function in peripheral nerve stumps of amputees: implications for neural control of artificial limbs. J Hand Surg Am 2004, 29(4):605-615
5. Abdelghani M N, Abbas J J, Horch K, Jung R: A computational model to simulate neural recordings from longitudinal intrafascicular electrodes. Society for Neuroscience Conference, 2012, 584.20/SS19
6. Hallin R G: Microneurography in relation to intraneural topography: somatotopic organization of median nerve fascicle in humans. J Neurol Neurosurg Psychiatry, 1990, 53:736-7-14
7. Lebedev, M A, Nicolelis, M A: Brain-machine interfaces: past, present and future. Trends in neurosciences, 2006, 29(9), 536-46
8. Velliste, M, Perel, S, Spalding, M C, Whitford, A S; Schwartz, A B: Cortical control of a prosthetic arm for self-feeding, 2008, Nature, 453, doi:10.1038/nature06996.
9. Musallam, S., Corneil, B D, Greger, B, Scherberger, H; Andersen, R A: Cognitive Control Signals for Neural Prosthetics. 2004, Science 305 (5681): 258-62. 2004 Sci . . . 305.258M. doi:10.1126/science.1097938. PMID 15247483.
10. Leigh R. Hochberg; Mijail D. Serruya, Gerhard M. Friehs, Jon A. Mukand, Maryam Saleh, Abraham H. Caplan, Almut Branner, David Chen, Richard D. Penn and John P. Donoghue (13 Jul. 2006). "Neuronal ensemble control of prosthetic devices by a human with tetraplegia". Nature 442 (7099): 164-171.
11. Yanagisawa, Takafumi (2011). "Electrocorticograpic Control of Prosthetic Arm in Paralyzed Patients". American Neurological Association. Retrieved 19 Jan. 2012. "ECoG-Based BCI has advantage in signal and durability that are absolutely necessary for clinical application
12. Navarro X, Krueger T B, Lago N, Micera S, Stieglitz T, Dario P. A critical review of interfaces with the peripheral nervous system for the control of neuroprostheses and hybrid bionic systems. J Peripher Nery Syst. 2005 September; 10(3):229-58.
13. Micera S, Navarro X: Bidirectional interfaces with the peripheral nervous system. Int Rev Neurobiol. 2009; 86:23-38. doi: 10.1016/S0074-7742(09)86002-9. Review.
14. Stieglitz T.: Neural prostheses in clinical practice: biomedical microsystems in neurological rehabilitation. Acta Neurochir Suppl. 2007; 97(Pt 1):411-8. Review.
15. Koch K P: Neural prostheses and biomedical microsystems in neurological rehabilitation. Acta Neurochir Suppl. 2007; 97(Pt 1):427-34. Review.
16. Micera S, Rigosa J, Carpaneto J, Citi L, Raspopovic S, Guglielmelli E, Benvenuto A, Rossini L, Di Pino G, Cavallo G, Carrozza M C, Cipriani C, Hoffmann K P, Dario P, Rossini P M.: On the control of a robot hand by extracting neural signals from the PNS: preliminary results from a human implantation. Conf Proc IEEE Eng Med Biol Soc. 2009; 2009:4586-9. doi: 10.1109/IEMBS.2009.5332764.
17. Santhanam G, Ryu S I, Yu B M, Afshar A, Shenoy K V: A high-performance brain-computer interface. Nature. 2006 Jul. 13; 442(7099):195-8.
18. U.S. Pat. No. 8,352,385
19. U.S. Pat. No. 7,442,212
20. U.S. Pat. No. 7,058,445
21. U.S. Provisional Pat. Application Ser. No. 61/714,578

What is claimed is:

1. A system comprising:
one or more electrodes recording intended motor actions from input signals;
at least one single channel decoder (SCD) in operable communication with the one or more electrodes and configured to decode the input signals; and
a demixer in operable communication with the at least one SCD and identifying, sorting, and segregating the decoded input signals of the at least one SCD as motor intent signals corresponding to a particular class of motor actions through use of a learning stage, the demixer being further configured to generate a set of control signals and to output the control signals to an external device, the control signals being based on the motor intent signals, and the control signals controlling the external device,
the input signals including at least one of neural signals and muscle signals,
the at least one SCD down-sampling and compressing the input signals, and the at least one SCD being configured to calculate an estimate of false positive rate by processing background noise after setting a threshold parameter and to use the estimate of false positive rate to reduce false positives during recording of the input signals and decoding of the input signals.

2. The system according to claim 1, wherein each SCD comprises:
   a filter configured to attenuate noise of the input signals and to sharpen spikes of the input signals corresponding to nerve firing;
   a detector configured to identify spikes of the input signals corresponding to the nerve firing; and
   a demodulator configured to generate an estimate of the motor intent signals.

3. The system according to claim 2, wherein the filter utilizes a nonlinear reshaping function to attenuate noise of the input signals and to sharpen spikes of the input signals corresponding to the nerve firing.

4. The system according to claim 2, wherein the demodulator is a single filter cascade of filters or a parallel set of filters, and wherein the demodulator is tunable such that it has a tunable time constant.

5. The system according to claim 1, wherein the at least one SCD outputs the decoded signals to the demixer, and wherein the demixer is configured to identify the motor intent signals as corresponding to a degree of movement of the intended motor actions.

6. The system according to claim 5, wherein the external device is a powered prosthesis, a television, a computer, a portable electronic device, a single degree-of-freedom robot, or a multiple degree-of-freedom robot.

7. The system according to claim 1, further comprising a decoder configuration unit configured to train the demixer to identify the decoded signals received from the at least one SCD as motor intent signals corresponding to a degree of movement of the intended motor actions.

8. The system according to claim 1, wherein the at least one SCD comprises a bank of bandpass filters configured to attenuate noise of the input signals and to sharpen spikes of the input signals corresponding to nerve firing.

9. A method comprising:
   receiving input signals by at least one single channel decoder (SCD) configured to decode the input signals;
   down-sampling and compressing the input signals by the at least one SCD;
   calculating, by the at least one SCD, an estimate of false positive rate by processing background noise after setting a threshold parameter;
   using, by the at least one SCD, the estimate of false positive rate to reduce false positives during recording of the input signals and decoding of the input signals;
   generating an estimate of the intended motor actions based on the decoded input signals;
   generating motor intent signals based on or comprising the generated estimate of the intended motor actions;
   outputting the motor intent signals to a demixer in operable communication with the at least one SCD;
   identifying, sorting, and segregating, by the demixer, the motor intent signals as corresponding to a particular class of motor actions through use of a learning stage, the input signals including at least one of neural signals and muscle signals; and
   generating, by the demixer, a set of control signals and outputting the control signals to an external device, the control signals being based on the motor intent signals, and the control signals controlling the external device.

10. The method according to claim 9, wherein each SCD comprises:
   a filter attenuating noise of the input signals and sharpening spikes of the input signals corresponding to nerve firing;
   a detector identifying spikes of the input signals corresponding to the nerve firing: and
   a demodulator generating the estimate of the motor intent signals.

11. The method according to claim 10, wherein the filter utilizes a nonlinear reshaping function to attenuate noise of the input signals and to sharpen spikes of the input signals corresponding to the nerve firing.

12. The method according to claim 10, wherein the demodulator is a single filter cascade of filters or a parallel set of filters, and wherein the demodulator is tunable such that it has a tunable time constant.

13. The method according to claim 9, wherein the demixer identifies the motor intent signals as corresponding to a degree of movement of the intended motor actions.

14. The method according to claim 13, wherein the external device is a powered prosthesis, a television, a computer, a portable electronic device, a single degree-of-freedom robot, or a multiple degree-of-freedom robot.

15. The method according to claim 9, further comprising training the demixer to identify the motor intent signals as corresponding to a degree of movement of the intended motor actions, wherein the demixer is trained by a decoder configuration unit.

16. The method according to claim 9, further comprising:
   recording the input signals by one or more electrodes in operable communication with the at least one SCD; and
   transmitting the input signals from the one or more electrodes to the at least one SCD.

17. A system comprising:
   one or more electrodes recording intended motor actions from input signals;
   at least one single channel decoder (SCD) in operable communication with the one or more electrodes and configured to decode the input signals;
   a demixer in operable communication with the at least one SCD and identifying, sorting, and segregating the decoded input signals of the at least one SCD as motor intent signals corresponding to a particular class of motor actions through use of a learning stage, the demixer being further configured to generate a set of control signals and to output the control signals to an external device, the control signals being based on the motor intent signals, and the control signals controlling the external device; and
   a decoder configuration unit providing an initialization parameter to the at least one SCD and training the demixer during a training phase of the demixer, the input signals including at least one of neural signals and muscle signals, each SCD comprising:
      a filter configured to attenuate noise of the input signals and to sharpen spikes of the input signals corresponding to nerve firing;
      a detector configured to identify spikes of the input signals corresponding to the nerve firing; and
      a demodulator configured to generate an estimate of the motor intent signals,
   the at least one SCD outputting the estimated motor intent signals to the demixer, and the demixer being configured to identify the estimated motor intent signals as corresponding to a degree of movement of the intended motor actions, each SCD down-sampling and compressing the input signals, and each SCD being configured to calculate an estimate of false positive rate by processing background noise after setting a threshold parameter and to use the estimate of false positive rate to reduce false positives during recording of the input signals and decoding of the input signals.

* * * * *